US009714269B2

United States Patent
Vreuls et al.

(10) Patent No.: US 9,714,269 B2
(45) Date of Patent: Jul. 25, 2017

(54) INORGANIC-BINDING PEPTIDES AND QUALITY CONTROL METHODS USING THEM

(75) Inventors: Christelle Vreuls, Blegny (BE); Cécile Van De Weerdt, Sprimont (BE); Catherine Archembeau, Esneux (BE); André Renard, Angleur (BE); Joseph Martial, Tilff (BE)

(73) Assignees: UNIVERSITE DE LIEGE INTERFACE ENTERPRISES UNIVERSITE, Angleur (BE); ARCELORMITTAL INVESTIGACIÓN Y DESARROLLO, S.L., Estao Bizkaia (ES); GESVAL S.A., Angleur (BE); SYMBIOSE BIOMATERIALS S.A., Liege (BE)

( * ) Notice: Subject to any disclaimer, the term of this patent is extended or adjusted under 35 U.S.C. 154(b) by 965 days.

(21) Appl. No.: 13/002,293

(22) PCT Filed: Jul. 6, 2009

(86) PCT No.: PCT/EP2009/004876
§ 371 (c)(1),
(2), (4) Date: Dec. 19, 2011

(87) PCT Pub. No.: WO2010/000493
PCT Pub. Date: Jan. 7, 2010

(65) Prior Publication Data
US 2013/0035245 A1  Feb. 7, 2013

Related U.S. Application Data

(60) Provisional application No. 61/090,300, filed on Aug. 20, 2008, provisional application No. 61/078,348, filed on Jul. 4, 2008.

(51) Int. Cl.
| | |
|---|---|
| G01N 33/20 | (2006.01) |
| C07K 7/08 | (2006.01) |
| C40B 30/04 | (2006.01) |
| G01N 21/64 | (2006.01) |
| G01N 27/72 | (2006.01) |
| G01N 21/76 | (2006.01) |
| G01N 21/78 | (2006.01) |

(52) U.S. Cl.
CPC .................................. C07K 7/08 (2013.01)

(58) Field of Classification Search
CPC ........................................................ G01N 33/20
USPC ............................................................ 506/9
See application file for complete search history.

(56) References Cited

U.S. PATENT DOCUMENTS

| 2002/0142473 A1 | 10/2002 | Lagraff et al. |
| 2007/0166350 A1* | 7/2007 | Hamilton et al. ........ A61F 2/02 424/423 |

FOREIGN PATENT DOCUMENTS

| EP | 0 266 032 | 8/1987 | |
| WO | WO 86/00031 | 3/1986 | |
| WO | WO 03026590 A2 * | 4/2003 | ............. B82Y 10/00 |
| WO | WO 03/078451 A2 | 9/2003 | |
| WO | WO 2006/045071 A2 | 4/2006 | |
| WO | WO 2007/081942 A2 | 7/2007 | |

OTHER PUBLICATIONS

Brown, "Metal-recognition by repeating polypeptides", Nature Biotechnology, vol. 15, p. 269-272 (1997).*
Tamerler and Sarikaya, "Molecular biomimetics: Utilizing nature's molecular ways in practical engineering", Acta Biomaterialia, vol. 3, p. 289-299 (2007).*
Sarikaya et al., Molecular Biomimetics: Nanotechnology Through Biology, Review Article, Nature Materials, 2003, 2, 577-585.*
Dickerson et al., Protein- and Peptide-Directed Synthesis of Inorganic Materials, Chem. Rev., 2008, 108, 4935-4978.*
Braasch et al., "Locked nucleic acid (LNA): fine-tuning the recognition of DNA and RNA," Chemistry & Biology (2001) 8: 1-7.
Brown et al., "Metal-recognition by repeating polypeptides," Nature Biotechnology (1997) 15: 269-272.
Chang et al., "High-level secretion of human growth hormone by Escherichia coli," Gene (1987) 55: 189-196.
Chen et al., "QCM-D analysis of binding mechanisms of phage particles displaying a constrained heptapeptide with specific affinity to $SiO_2$ and $TiO_2$," Anal. Chem. (2006) 78: 4872-4879.
Engels et al., "Gene Syntheis," Angew. Chem. Int. Ed. Engl. (1989) 28: 716-734.
Enshell-Seijffers et al., "The rational design of a 'type 88' genetically stable peptide display vector in the filamentous bacteriophage fd," Nucleic Acids Research (2001) 29 (10 e50): 1-13.
Froehler et al., "Synthesis of DNA via deoxynulceoside H-phosphate intermediates," Nucleic Acids Research (1986) 14 (13): 5399-5407.
Gaskin et al., "Identification of inorganic crystal-specific sequences using phage display combinatorial library of short peptides: A feasibility study," Biotechnology Letters (2000) 22: 1211-1216.

(Continued)

Primary Examiner — Amy M Bunker
(74) Attorney, Agent, or Firm — Merchant & Gould P.C.

(57) ABSTRACT

The present invention relates to quality control methods using inorganic binding peptides, wherein inorganic entities are identified using inorganic-binding peptides specifically binding to the inorganic entity of interest. In particular, the invention includes a method for the identification of defects or inhomogeneities on a surface by detecting an inorganic entity of interest. It further includes a method for the isolation of powder particles comprising an inorganic entity of interest from a mixture of powder particles. In addition, the present invention relates to inorganic-binding peptides comprising the amino acid sequence MTWDPSLASPRS (SEQ ID NO: 31) and the amino acid sequence LNAAVP-FTMAGS (SEQ ID NO: 32), respectively.

4 Claims, 6 Drawing Sheets

(56) References Cited

OTHER PUBLICATIONS

Figure 1:
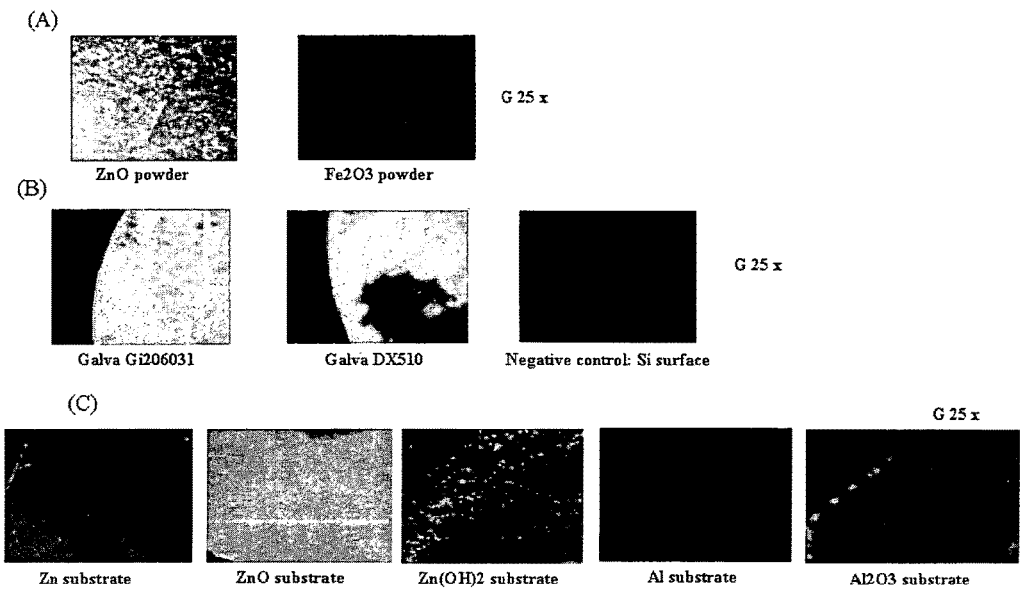

General method for the rapid solid-phase synthesis of large numbers of peptides: Specificity of antigen-antibody interaction at the level of individual amino acids, *Proc. Natl. Acad. Sci.* (1985) 82: 5131-5135.

Hufton et al., "Phage display of cDNA repertoires: the pVI display system and its applications for the selection of immunogenic ligands," *Journal of Immunological Methods* (1999) 231: 39-51.

Jószai et al., "Transition metal complexes of terminally protected peptides containing histidyl residues," *Journal of Inorganic Biochemistry* (2006) 100: 1399-1409.

Kjaergaard et al., "Sequestration of zinc oxide by fimbrial designer chelators," *Applied and Enviornmental Microbiology* (2000) 66 (1): 10-14.

Lowman et al., "Monovalent phage display: A method for selecting variant proteins from random libraries," *METHODS: A Comparison to Methods in Enzymology* (1991) 3 (3): 205-216.

Mao et al., "Viral assembly of oriented quantum dot nanowires," *PNAS* (2003) 100 (12): 6946-6951.

Merrifield, R.B., "Solid phase peptide synthesis. I. The synthesis of a tetrapeptide," *J. Am. Chem. Soc.* (1963) 85 (14): 2149-2154.

Naik et al., "Silica-precipitating peptides isolated froma combinatorial phage display peptide library," *Journal of Nanoscience and Nanotechnology* (2002) 2 (1): 95-100.

Oren et al., "Metal recognition of septapeptides via polypod molecular architecture," *Nano Letters* (2005) 5 (3): 415-419.

Pereboev et al., "Phage display of adenovirus type 5 fiber knob as a tool for specific ligand selection and validation," *Journal of Virology* (2001) 75 (15): 7107-7113.

Rondot et al., "A helper to improve single-chain antibody presentation in phage display," *Nature Biotechnology* (2001) 19: 75-78.

Sanghvi et al., "Biomaterials functionalization using a novel peptide that selectively binds to a conducting polymer," *Nature Materials* (2005) 4: 496-502.

Sano et al., "A hexapeptide motif that electrostatically binds to the surface of titanium," *J. Am. Chem. Soc.* (2003) 125: 14234-14235.

Schembri et al., "Bioaccumulation of heavy metals by fimbrial designer adhesins," *FEMS Microbiology Letters* (1999) 170:363-371.

Tamerler et al., "Molecular biometrics: Utilizing nature's molecular ways in practical engineering," *Acta Biomaterialia* (2007) 3: 289-299.

Wang et al., "Peptides with selective affinity for carbon nanotubes," *Nature Materials* (2003) 21: 196-200.

Weiss et al., "Mutational analysis of the major coat protein of M13 identifies residues that control protein display," *Protein Science* (2009) 9: 647-654.

Wells et al., "Rapid evolution of peptide and protein binding properties in vitro," *Current Opinion in Biotechnology* (1992) 3: 355-362.

Whaley et al., "Selection of peptides with semiconductor binding specificity for directed nanocrystal assembly," *Nature* (2000) 405: 665-668.

Wong et al., "Expression of secreted insulin-like growth factor-1 in *Escherichia coli*," *Gene* (1988) 68: 193-203.

Xu et al., "Biomimetic synthesis silver crystallite by peptide AYS-SGAPPMPPF immobilized on PET film in vitro," *Journal of Inorganic Biochemistry* (2005) 99: 1692-1697.

Zuo et al., "Aluminum-and mild steel-binding peptides from phage display," *Appl. Microbiol. Biotechnol.* (2005) 68: 505-509.

Form PCT/ISA/210 for corresponding International Application No. PCT/EP2009/004876.

Form PCT/ISA/237 for corresponding International Application No. PCT/EP2009/004876.

\* cited by examiner

| XPS analyses of Galva Gi206031 substrate in binding buffer | C1s (% at) | N1s (% at) | O1s (% at) | Al2p (% at) | Ca2p3 (% at) | Cu2p3 (% at) | Zn2p3 (% at) |
|---|---|---|---|---|---|---|---|
| Untreated substrate | 61,81 | 0,78 | 24,07 | 9,54 | 0,17 | 0 | 2,55 |
| Ungreased substrate | 46,08 | 1,44 | 33,39 | 0,7 | 0,26 | 0,45 | 15,92 |
| Ungreased and heated substrate | 50,51 | 0,51 | 28 | 0,23 | 0 | 0 | 19,55 |

GEPI ZnO – Galva Gi206031
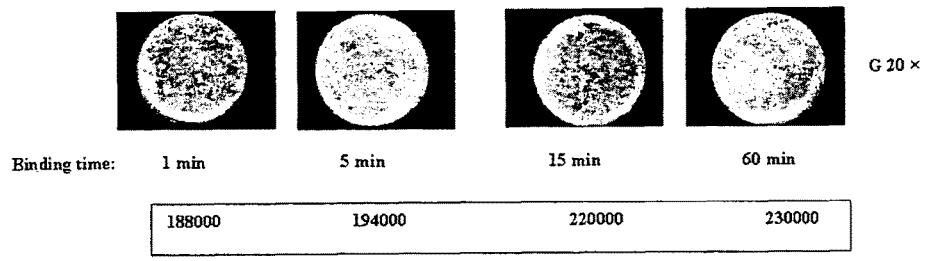
| Binding time: | 1 min | 5 min | 15 min | 60 min |
|---|---|---|---|---|
| | 188000 | 194000 | 220000 | 230000 |
GEPI ZnO – Galva Gi206031
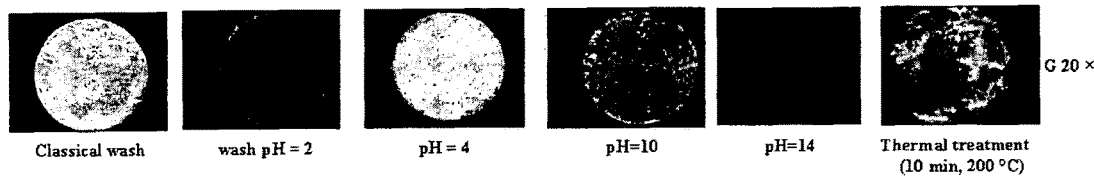
Classical wash | wash pH = 2 | pH = 4 | pH=10 | pH=14 | Thermal treatment (10 min, 200 °C)
Figure 3
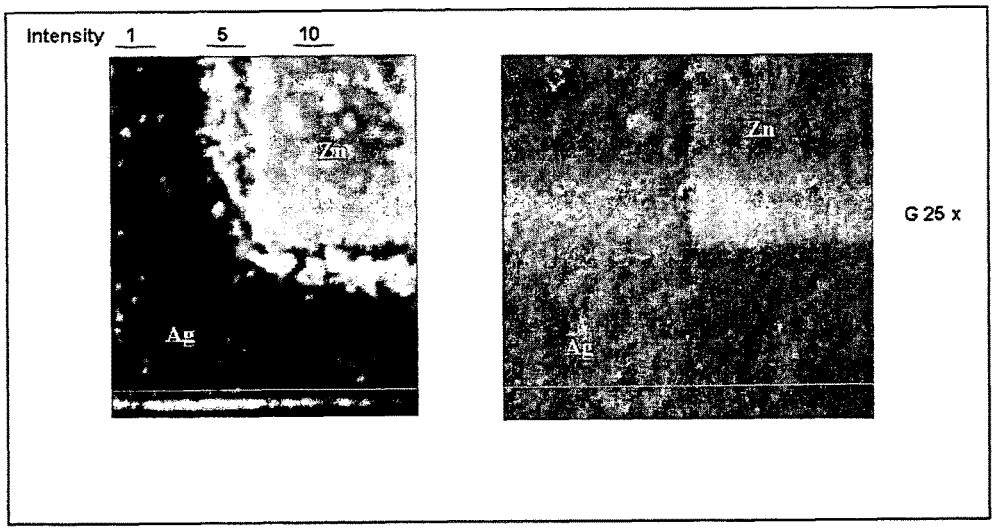
Figure 4

| Phage number | Start | Round 1 | Round 2 | Round 3 | Round 4 |
|---|---|---|---|---|---|
| Stainless steel substrate | $2,7.10^9$ | $10^7$ | $2.10^5$ | $5.10^3$ | 100 |
| TiO2 substrate | $2,7.10^9$ | $10^7$ | $2.10^5$ | 100 | < 100 |

Diminution of library diversity round by round

Enrichissement in consensus sequence

Consensus sequence for stainless steel after 4 rounds of selection:
MTWDPSLASPRS (SEQ ID NO:31)

Consensus sequence for TiO$_2$ after 4 rounds of selection:
LNAAVPFTMAGS (SEQ ID NO:32)

Figure 5

(A)

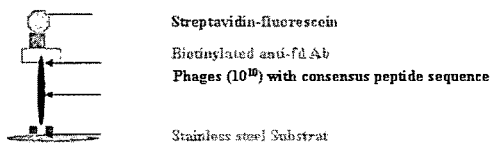

Streptavidin-fluorescein
Biotinylated anti-fd Ab
Phages ($10^{10}$) with consensus peptide sequence Stainless steel Substrat (B) G 20 x

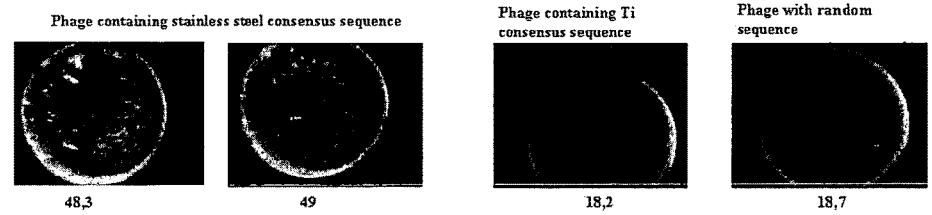

Phage containing stainless steel consensus sequence     Phage containing Ti consensus sequence     Phage with random sequence 48,3     49     18,2     18,7

(C)

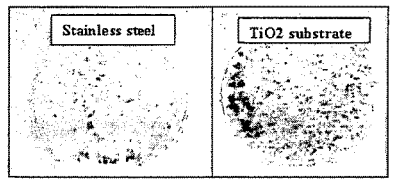

Stainless steel     TiO2 substrate

Figure 6

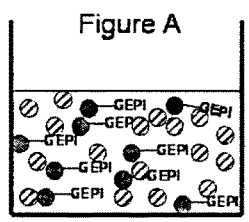
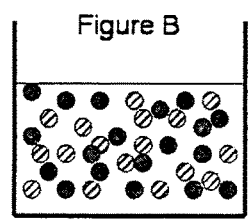
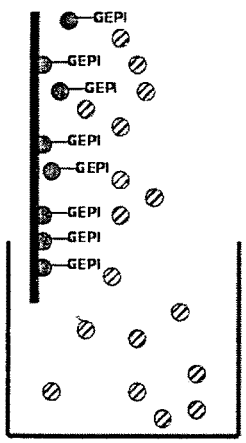
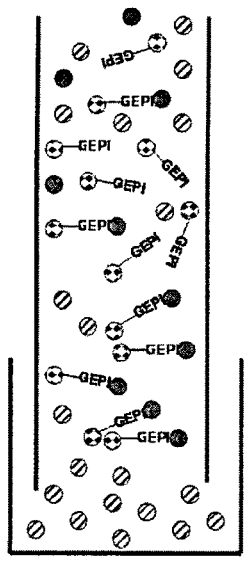
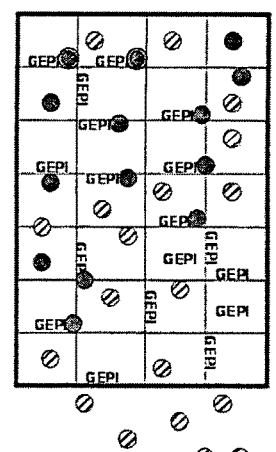
Figure 11

SEQUENCE LISTING

```
<160> NUMBER OF SEQ ID NOS: 32

<210> SEQ ID NO 1
<211> LENGTH: 14
<212> TYPE: PRT
<213> ORGANISM: Artificial sequence
<220> FEATURE:
<223> OTHER INFORMATION: /note="Description of artificial sequence:
      inorganic-binding peptide"

<400> SEQUENCE: 1

Met His Gly Lys Thr Gln Ala Thr Ser Gly Thr Ile Gln Ser
1               5                   10
```

```
<210> SEQ ID NO 2
<211> LENGTH: 21
<212> TYPE: PRT
<213> ORGANISM: Artificial sequence
<220> FEATURE:
<223> OTHER INFORMATION: /note="Description of artificial sequence:
      inorganic-binding peptide"

<400> SEQUENCE: 2

Ser Lys Thr Ser Leu Gly Gln Ser Gly Ala Ser Leu Gln Gly Ser Glu
1               5                   10                  15

Lys Leu Thr Asn Gly
            20

<210> SEQ ID NO 3
<211> LENGTH: 7
<212> TYPE: PRT
<213> ORGANISM: Artificial sequence
<220> FEATURE:
<223> OTHER INFORMATION: /note="Description of artificial sequence:
      inorganic-binding peptide"

<400> SEQUENCE: 3

Asp Arg Thr Ser Thr Trp Arg
1               5

<210> SEQ ID NO 4
<211> LENGTH: 7
<212> TYPE: PRT
<213> ORGANISM: Artificial sequence
<220> FEATURE:
<223> OTHER INFORMATION: /note="Description of artificial sequence:
      inorganic-binding peptide"

<400> SEQUENCE: 4

Gln Ser Val Thr Ser Thr Lys
1               5

<210> SEQ ID NO 5
<211> LENGTH: 7
<212> TYPE: PRT
<213> ORGANISM: Artificial sequence
<220> FEATURE:
<223> OTHER INFORMATION: /note="Description of artificial sequence:
      inorganic-binding peptide"

<400> SEQUENCE: 5

Ser Val Thr Gln Asn Lys Tyr
1               5

<210> SEQ ID NO 6
<211> LENGTH: 7
<212> TYPE: PRT
<213> ORGANISM: Artificial sequence
<220> FEATURE:
<223> OTHER INFORMATION: /note="Description of artificial sequence:
      inorganic-binding peptide"

<400> SEQUENCE: 6

Ser Pro His Pro Gly Pro Tyr
1               5

<210> SEQ ID NO 7
<211> LENGTH: 12
<212> TYPE: PRT
<213> ORGANISM: Artificial sequence
```

```
<220> FEATURE:
<223> OTHER INFORMATION: /note="Description of artificial sequence:
      inorganic-binding peptide"

<400> SEQUENCE: 7

Val Pro Ser Ser Gly Pro Gln Asp Thr Gly Thr Thr
1               5                   10

<210> SEQ ID NO 8
<211> LENGTH: 12
<212> TYPE: PRT
<213> ORGANISM: Artificial sequence
<220> FEATURE:
<223> OTHER INFORMATION: /note="Description of artificial sequence:
      inorganic-binding peptide"

<400> SEQUENCE: 8

Ala Tyr Ser Ser Gly Ala Pro Pro Met Pro Pro Phe
1               5                   10

<210> SEQ ID NO 9
<211> LENGTH: 12
<212> TYPE: PRT
<213> ORGANISM: Artificial sequence
<220> FEATURE:
<223> OTHER INFORMATION: /note="Description of artificial sequence:
      inorganic-binding peptide"

<400> SEQUENCE: 9

Asn Pro Ser Ser Leu Phe Arg Tyr Leu Pro Ser Asp
1               5                   10

<210> SEQ ID NO 10
<211> LENGTH: 12
<212> TYPE: PRT
<213> ORGANISM: Artificial sequence
<220> FEATURE:
<223> OTHER INFORMATION: /note="Description of artificial sequence:
      inorganic-binding peptide"

<400> SEQUENCE: 10

Met Ser Pro His Pro His Pro Arg His His His Thr
1               5                   10

<210> SEQ ID NO 11
<211> LENGTH: 12
<212> TYPE: PRT
<213> ORGANISM: Artificial sequence
<220> FEATURE:
<223> OTHER INFORMATION: /note="Description of artificial sequence:
      inorganic-binding peptide"

<400> SEQUENCE: 11

Arg Gly Arg Arg Arg Arg Leu Ser Cys Arg Leu Leu
1               5                   10

<210> SEQ ID NO 12
<211> LENGTH: 12
<212> TYPE: PRT
<213> ORGANISM: Artificial sequence
<220> FEATURE:
<223> OTHER INFORMATION: /note="Description of artificial sequence:
      inorganic-binding peptide"

<400> SEQUENCE: 12

Lys Pro Ser His His His His Thr Gly Ala Asn
1               5                   10
```

-continued

```
<210> SEQ ID NO 13
<211> LENGTH: 21
<212> TYPE: PRT
<213> ORGANISM: Artificial sequence
<220> FEATURE:
<223> OTHER INFORMATION: /note="Description of artificial sequence:
      inorganic-binding peptide"

<400> SEQUENCE: 13

Val Lys Thr Gln Ala Thr Ser Arg Glu Glu Pro Pro Arg Leu Pro Ser
1               5                   10                  15

Lys His Arg Pro Gly
            20

<210> SEQ ID NO 14
<211> LENGTH: 14
<212> TYPE: PRT
<213> ORGANISM: Artificial sequence
<220> FEATURE:
<223> OTHER INFORMATION: /note="Description of artificial sequence:
      inorganic-binding peptide"

<400> SEQUENCE: 14

Met Asp His Gly Lys Tyr Arg Gln Lys Gly Ala Thr Pro Gly
1               5                   10

<210> SEQ ID NO 15
<211> LENGTH: 16
<212> TYPE: PRT
<213> ORGANISM: Artificial sequence
<220> FEATURE:
<223> OTHER INFORMATION: /note="Description of artificial sequence:
      inorganic-binding peptide"

<400> SEQUENCE: 15

Asn Thr Arg Met Thr Ala Arg Gln His Ala Asn His Lys Ser Thr Gln
1               5                   10                  15

<210> SEQ ID NO 16
<211> LENGTH: 12
<212> TYPE: PRT
<213> ORGANISM: Artificial sequence
<220> FEATURE:
<223> OTHER INFORMATION: /note="Description of artificial sequence:
      inorganic-binding peptide"

<400> SEQUENCE: 16

Val Arg Thr Arg Asp Asp Ala Arg Thr His Arg Lys
1               5                   10

<210> SEQ ID NO 17
<211> LENGTH: 12
<212> TYPE: PRT
<213> ORGANISM: Artificial sequence
<220> FEATURE:
<223> OTHER INFORMATION: /note="Description of artificial sequence:
      inorganic-binding peptide"

<400> SEQUENCE: 17

His Thr Gln Asn Met Arg Met Tyr Glu Pro Trp Phe
1               5                   10

<210> SEQ ID NO 18
<211> LENGTH: 12
<212> TYPE: PRT
<213> ORGANISM: Artificial sequence
```

```
<220> FEATURE:
<223> OTHER INFORMATION: /note="Description of artificial sequence:
      inorganic-binding peptide"

<400> SEQUENCE: 18

Asp Val Phe Ser Ser Phe Asn Leu Lys His Met Arg
1               5                   10

<210> SEQ ID NO 19
<211> LENGTH: 9
<212> TYPE: PRT
<213> ORGANISM: Artificial sequence
<220> FEATURE:
<223> OTHER INFORMATION: /note="Description of artificial sequence:
      inorganic-binding peptide"

<400> SEQUENCE: 19

Val Val Arg Pro Lys Ala Ala Thr Asn
1               5

<210> SEQ ID NO 20
<211> LENGTH: 9
<212> TYPE: PRT
<213> ORGANISM: Artificial sequence
<220> FEATURE:
<223> OTHER INFORMATION: /note="Description of artificial sequence:
      inorganic-binding peptide"

<400> SEQUENCE: 20

Arg Ile Arg His Arg Leu Val Gly Gln
1               5

<210> SEQ ID NO 21
<211> LENGTH: 12
<212> TYPE: PRT
<213> ORGANISM: Artificial sequence
<220> FEATURE:
<223> OTHER INFORMATION: /note="Description of artificial sequence:
      inorganic-binding peptide"

<400> SEQUENCE: 21

Arg Lys Leu Pro Asp Ala Pro Gly Met His Thr Trp
1               5                   10

<210> SEQ ID NO 22
<211> LENGTH: 9
<212> TYPE: PRT
<213> ORGANISM: Artificial sequence
<220> FEATURE:
<223> OTHER INFORMATION: /note="Description of artificial sequence:
      inorganic-binding peptide"

<400> SEQUENCE: 22

Cys His Lys Lys Pro Ser Lys Ser Cys
1               5

<210> SEQ ID NO 23
<211> LENGTH: 9
<212> TYPE: PRT
<213> ORGANISM: Artificial sequence
<220> FEATURE:
<223> OTHER INFORMATION: /note="Description of artificial sequence:
      inorganic-binding peptide"

<400> SEQUENCE: 23

Arg Arg Thr Val Lys His His Val Asn
1               5
```

```
<210> SEQ ID NO 24
<211> LENGTH: 13
<212> TYPE: PRT
<213> ORGANISM: Artificial sequence
<220> FEATURE:
<223> OTHER INFORMATION: /note="Description of artificial sequence:
      inorganic-binding peptide"

<400> SEQUENCE: 24

Ala Gln Asn Pro Ser Asp Asp Asn Asn Thr His Thr His
1               5                   10

<210> SEQ ID NO 25
<211> LENGTH: 12
<212> TYPE: PRT
<213> ORGANISM: Artificial sequence
<220> FEATURE:
<223> OTHER INFORMATION: /note="Description of artificial sequence:
      inorganic-binding peptide"

<400> SEQUENCE: 25

Arg Leu Glu Leu Ala Ile Pro Leu Gln Gly Ser Gly
1               5                   10

<210> SEQ ID NO 26
<211> LENGTH: 12
<212> TYPE: PRT
<213> ORGANISM: Artificial sequence
<220> FEATURE:
<223> OTHER INFORMATION: /note="Description of artificial sequence:
      inorganic-binding peptide"

<400> SEQUENCE: 26

Thr Pro Pro Arg Pro Ile Gln Tyr Asn His Thr Ser
1               5                   10

<210> SEQ ID NO 27
<211> LENGTH: 7
<212> TYPE: PRT
<213> ORGANISM: Artificial sequence
<220> FEATURE:
<223> OTHER INFORMATION: /note="Description of artificial sequence:
      inorganic-binding peptide"

<400> SEQUENCE: 27

Asn Asn Pro Met His Gln Asn
1               5

<210> SEQ ID NO 28
<211> LENGTH: 12
<212> TYPE: PRT
<213> ORGANISM: Artificial sequence
<220> FEATURE:
<223> OTHER INFORMATION: /note="Description of artificial sequence:
      inorganic-binding peptide"

<400> SEQUENCE: 28

His Trp Ser Ala Trp Trp Ile Arg Ser Asn Gln Ser
1               5                   10

<210> SEQ ID NO 29
<211> LENGTH: 12
<212> TYPE: PRT
<213> ORGANISM: Artificial sequence
<220> FEATURE:
<223> OTHER INFORMATION: /note="Description of artificial sequence:
      inorganic-binding peptide"
```

```
<400> SEQUENCE: 29

Thr His Arg Thr Ser Thr Leu Asp Tyr Phe Val Ile
1               5                   10

<210> SEQ ID NO 30
<211> LENGTH: 20
<212> TYPE: DNA
<213> ORGANISM: Artificial sequence
<220> FEATURE:
<223> OTHER INFORMATION: /note="Description of artificial sequence:
      inorganic-binding peptide"

<400> SEQUENCE: 30
ccctcatagt tagcgtaacg                                                    20

<210> SEQ ID NO 31
<211> LENGTH: 12
<212> TYPE: PRT
<213> ORGANISM: Artificial sequence
<220> FEATURE:
<223> OTHER INFORMATION: /note="Description of artificial sequence:
      inorganic-binding peptide"

<400> SEQUENCE: 31

Met Thr Trp Asp Pro Ser Leu Ala Ser Pro Arg Ser
1               5                   10

<210> SEQ ID NO 32
<211> LENGTH: 12
<212> TYPE: PRT
<213> ORGANISM: Artificial sequence
<220> FEATURE:
<223> OTHER INFORMATION: /note="Description of artificial sequence:
      inorganic-binding peptide"

<400> SEQUENCE: 32

Leu Asn Ala Ala Val Pro Phe Thr Met Ala Gly Ser
1               5                   10
```

US 9,714,269 B2

INORGANIC-BINDING PEPTIDES AND QUALITY CONTROL METHODS USING THEM

CROSS-REFERENCE TO RELATED APPLICATIONS

This application is a national stage entry under 35 U.S.C. §371 of PCT/EP2009/004876, filed Jul. 6, 2009, which claims the benefit under 35 U.S.C. §119(e) of U.S. Provisional Application No. 61/090,300, filed Aug. 20, 2008, and which also claims benefit of U.S. Provisional Application No. 61/078,348, filed Jul. 4, 2008, the entire disclosures of which are hereby incorporated by reference.

The present invention relates to quality control methods using inorganic binding peptides, wherein inorganic entities of interest are identified using inorganic-binding peptides specifically binding thereto. In particular, the invention includes a method for the identification of defects or inhomogenieties on a surface by detecting an inorganic entity of interest. It further includes a method for the isolation of powder particles comprising an inorganic entity of interest from a mixture of powder particles. In addition, the present invention relates to inorganic-binding peptides comprising the amino acid sequence MTWDPSLASPRS (SEQ ID NO: 31) and the amino acid sequence LNAAVPFTMAGS (SEQ ID NO: 32), respectively.

The rapidly emerging field of biomimetic materials forms one of the most important technologies of the 21$^{st}$ century. Biomimetic materials seek to replicate and mimic inorganic and organic materials as well as biological processes. A better understanding of how living organisms produce minerals and composites ensures the creation of new industrial processes. In this context, materials can be fabricated much more precisely and efficiently, resulting in new functionalities and increased performance. For example, the observation that organisms use proteins or peptides to control nucleation, assembly and architecture of inorganic phases has opened the door to new applications. Indeed, inorganic-binding peptides could be used as molecular erector sets to direct the assembly of hybrid materials with control of composition and topography. With the objective to extend these properties of inorganic-binding peptides to selected materials of interest, many efforts have been directed at identifying small peptides that bind with high affinity to inorganic materials. These peptides are called GEPI for "genetically engineered polypeptide for inorganics". They are defined as a sequence of amino acids that specifically and selectively binds to an inorganic surface. Whereas the molecular mechanisms of peptide recognition and binding to solid materials are not well understood, some studies showed that the binding is largely governed by electrostatic interaction. For titane-binding peptides for example, it has been proven that the specific binding is due to double electrostatic bonds between charged amino-acids residues and surface groups of the substrate (Chen, 2006).

An advantage of inorganic-binding peptides is their high specificity that depends on (i) the chemical composition, (ii) the structuration (powder or flat surface) and the (iii) crystallographic form of the inorganic target substrate. This specificity gives them interesting properties and several applications have already been highlighted (Tamerler, 2007). Inorganic-binding peptides display useful characteristics and could be used as molecular erectors to direct the assembly of hybrid materials with control of composition and topography. Several applications have been highlighted. For instance, engineered viruses appear very useful as templates for nanostucturation of nanowires (Mao, 2003). Genetic fusion of these inorganic-binding peptides to functional proteins enables them to be used as linkers for many bio-nanotechnological or microelectronic applications (Brown, 1997, Tamerler, 2007, Whaley, 2000). Inorganic-binding peptides may also be used for self-oriented immobilization of enzymes with conservation of their enzymatic activity. A fivefold repeat of gold binding-peptide has been fused to the alkaline phosphatase enzyme. The resulting bifunctional enzyme is then self-immobilized, homogenously covering the gold substrate. The utilization of the GEPI's ability to selectively bind a specific inorganic substrate could also allow the development of a new virus phage and cell sorting platforms using micro-patterned substrates (Dincer). Schembri also highlights the use of inorganic-binding peptides as biosorption agents for the removal of toxic or precious metals from the environment (Schembri, 1999).

The present invention provides methods as defined in the annexed claims which rely on the above characteristics of inorganic binding peptides in order to efficiently characterize specific types of surfaces comprising inorganic entities of interest. In addition, the invention provides novel peptides specifically binding to certain inorganic substrates.

Thus, the present invention includes in a first aspect a method using inorganic binding peptides as quality control tools for defect detection on inorganic surfaces of any shapes. An embodiment of the quality control method includes characterization of an inorganic surface on a production line, and not removing the inorganic surface to be characterized from the production line. The method can include dipping an inorganic surface into a peptide solution and observing the surface under fluorescence. An inorganic surface coated with a binding peptide can be visualized by eye under a simple fluorescent lamp or by microscopic analyses under fluorescence.

In particular, this first aspect of the present invention concerns a method for the identification of defects or inhomogenieties on a surface by detecting an inorganic entity of interest, comprising the steps of:

(a) contacting the surface with an inorganic-binding peptide carrying a detectable marker and being capable of specifically binding to the inorganic entity of interest;

(b) removing unbound peptide; and (c) detecting the peptide remaining on the surface.

The present invention also includes a method of isolating powders from powder mixtures. For example, an embodiment of this second aspect of the invention includes a method of sorting powders, especially nanopowders, wherein a nanopowder is contacted with an inorganic binding peptide and sorted by at least one of chemical composition, morphology, or crystallographic form.

A method embodying this second aspect of the invention is a method for the isolation of powder particles comprising an inorganic entity of interest from a mixture of powder particles, comprising the steps of:

(a) contacting the powder with an inorganic-binding peptide capable of specifically binding to the inorganic entity of interest, and (b) isolating the powder particles to which the inorganic binding peptide has bound.

The present invention also includes novel inorganic-binding peptides. Novel inorganic-binding peptides of the invention include a stainless steel binding peptide MTWDPSLASPRS (SEQ ID NO: 31) and a TiO$_2$ binding peptide LNAAVPFTMAGS (SEQ ID NO: 32).

DETAILED DESCRIPTION OF THE INVENTION

The term "inorganic-binding peptide", as used herein, relates to peptides that specifically bind to/interact with an inorganic entity which is characterized by its chemical composition, morphology, or crystallographic form. The term "inorganic-binding peptide" is understood to include both naturally occurring peptides having the ability to selectively bind to/interact with an inorganic material as well as synthetically produced peptides, such as genetically engineered peptides for inorganics (GEPI), which can be selected, for example via directed evolution and through combinatorial biology based peptide libraries, and which may have undergone post-selection modifications through genetic engineering.

The inorganic-binding peptides described in the context of the invention are capable of specifically binding to or specifically interacting with an inorganic entity of interest, in particular entities that are accessible on the surface of inorganic materials or surfaces comprising inorganic materials. The term "specifically binding to or interacting with" as used in accordance with the present invention means that the inorganic-binding peptide does not or essentially does not cross-react with other inorganic entities. Cross-reactivity of a panel of inorganic-binding peptides under investigation may be tested, for example, by assessing binding of said panel of inorganic-binding peptides under conventional conditions to the inorganic surface structure of interest as well as to a number of more or less (structurally and/or functionally) closely related inorganic surface structures. Only those inorganic-binding peptides that bind to the inorganic entity of interest but do not or do essentially not bind to any of the other inorganic surface structures are considered specific for the inorganic entity of interest and thus to be inorganic-binding peptides in accordance with this invention. The specific binding of the inorganic-binding peptide to the inorganic entity of interest is typically the result of a complex combination of long and short range interaction forces as well as a contribution of the structure and the spatial arrangement of the peptide on the top layer of an inorganic surface or a surface comprising an inorganic material.

The inorganic-binding peptide is generally a neutral peptide, preferably neutralized at its C-terminal. Neutralisation of the inorganic-binding peptide can be carried out by any neutralisation processes known in the art. In a more preferred embodiment, the neutralisation is carried out by amidation, e.g. by reaction with an amide, preferably an alkylamide, to form a group such as —CONHR or esterification, e.g. with alkyl alcohols, to form a group —COOR. In an even more preferred embodiment, the neutralisation is achieved by amidation.

Advantageously, the methods according to the invention can be carried out without working with phages after suitable inorganic-binding peptides have been identified, thus avoiding, e.g. widespread dispersion of phages. This is one of the advantages which allow a large scale application of the methods according to the invention in an industrial context.

As noted above, the invention relates in a first aspect to a method for the identification of defects and/or inhomogeneities on a surface by detecting an inorganic entity of interest, comprising the steps of:

(a) contacting the surface with an inorganic-binding peptide carrying a detectable marker and being capable of specifically binding to the inorganic entity of interest;
(b) removing unbound peptide; and
(c) detecting the peptide remaining on the surface.

The method referred to in this aspect is typically a method of quality control, in particular surface quality control. The method allows for a convenient control of surface preparation (i.e. whether a surface has been correctly prepared), control of the quality of the surface or control of the quality of a coating on a surface. Thus, the method may be a method of quality control as it is used as a step in the production of inorganic materials. It is useful, e.g., in the production of metals or products made of metal, such as steel inclusive of stainless steel, or various other alloys. It is also useful in the context of the production of coatings for inorganic materials or inorganic coatings for various materials, e.g. in the production of microelectronics or nanosensors, or for the painting of surfaces, e.g. in the automobile industry.

As a specific example, the method allows to examine whether the cleaning of a surface has been carried out properly. In the case of galvanized steel surface, for example, an inorganic binding peptide binding to ZnO can detect if the prior alkaline cleaning step has been performed properly and has removed the unwanted alumina layer. Areas where no peptide has bound to and cannot be detected on the surface indicate that alumina remains on the galvanized steel surface.

Conveniently, the method according to the invention can be practiced as an in-line method which forms a part of a production or coating process, i.e. the products to be subjected to the method do not have to be removed from the production/coating line.

The term "defects" includes, without being limiting, impurities which may be present on a surface or impurities incorporated a surface, e.g. defects in the chemical composition of a material providing the surface under consideration. Inhomogenieties include inhomogeneous distributions of an inorganic entity of interest within the surface, e.g. in the case of alloys, where inorganic components of the alloy may not be homogenously spread throughout the alloy material, or the inhomogeneous coverage of a surface by a coating, e.g. the presence of unwanted non-coated areas, formation of coating defects such as pinholes.

Surfaces on which the method of the invention can be practiced are not particularly limited. They include surfaces of metals and non-metals, especially metals, semiconducting materials, and oxides of the metals and semiconducting materials. Often, the surface comprises or consists of at least one material selected from the group consisting of aluminium, antimony, beryllium, cadmium, copper, chrome, gold, iron, lead, selenium, palladium, platinum, stainless steel, titanium, zinc, silicium, germanium and oxides of these. Surfaces can have various shapes, often the surfaces are planar. Preferred surface materials comprise or consist of aluminium, copper, iron, silver, palladium, platinum, zinc, and oxides of these materials or alloys including these metals, and in particular steel, inclusive of stainless steel. Surfaces to which the process of the invention can be applied also include coated surfaces, especially coated inorganic materials or surfaces carrying an inorganic coating. Such inorganic coatings may be present on various materials including metals, but also glass or on organic polymers or plastics. Exemplary coatings are coatings comprising or consisting of a metal oxide such as titanium oxide or aluminium oxide, coatings comprising or consisting of a metal such as silver, platinum, palladium, aluminium or copper, or coatings comprising or consisting of semiconducting materials such as silicon or silicon oxide or germanium or germanium oxide. Inter alia, coatings envisaged for the coated surfaces in the context of the invention are inorganic coated steal surfaces including zinc oxide coatings as applied in the galvanization of steel, or inorganic coatings, specifically metal or metal oxide coatings, as applied by physical or chemical vapour deposition methods (PVD, CVD).

As will be understood, surfaces and coated surfaces may be subjected to the method according to the invention in various forms, including sheets, plates, panels and slabs. Surfaces of interest also include electronic parts, such as printed circuits, or nanosensors. The inherent versatility of the method according to the invention allows surfaces of various sized to be subjected to the above methods, such as for example surfaces which are in the range of square microns to square meters. For example, the invention may be conveniently practiced on surfaces of 1 $\mu m^2$ or more, 1 $mm^2$ or more, 1 $cm^2$ or more, 100 $cm^2$ or more or even 1000 $cm^2$ or more.

In the context of this document, reference is sometimes made to substrates which are subjected to the methods of the invention. It will be understood that these substrates are broadly the materials, products, coated materials, etc. on which the surfaces are found where defects and/or inhomogeneities are to be identified.

The term "identification" as used in the context of the invention broadly includes both (i) showing the presence or the absence of defects or inhomogeneities and (ii) the localization of defects or inhomogeneities on the surface under consideration. It should be understood that the identification of defects or inhomogeneities includes a variety of possible strategies, such as a) the detection of an inorganic entity which is known or suspected to form an impurity on/within the surface, such that the detection directly identifies the impurities, b) the detection of an inorganic entity which forms the main component or one of the main components of the surface, such that the detection identifies those parts of the surface which do not contain defects or inhomogeneities, c) the detection of an inorganic entity forming or comprised in a material which carries a coating, such that the detection indicates those parts of the surface which are not covered by the coating, and d) the detection of an inorganic entity forming or comprised in a coating, such that the detection indicates those parts of the surface which are properly covered by the coating.

The inorganic entity or inorganic entity of interest includes an inorganic compound which is characterized by its chemical composition, e.g. a metal, a metal oxide, a semiconductor or a non metal. Suitable compounds include those mentioned as inorganic materials or inorganic coatings for surfaces above, thus often the inorganic entity is selected from aluminium, antimony, beryllium, cadmium, copper, chrome, gold, iron, lead, selenium, palladium, platinum, titanium, zinc, silicon, germanium and oxides thereof, particularly from $TiO_2$, $ZnO$, $Al_2O_3$, or from steel, inclusive of stainless steel, or carbon. However, the inorganic entity may also be characterized by its crystallographic form, e.g. crystalline, amorphous, or by specific crystal forms.

It will be understood that the inorganic entities of interest referred to in the context of the invention are typically entities which are present at or near the surface of a substrate, preferably at the surface.

Detectable markers which can be used in the context of the invention are not particularly limited. They include markers selected from the group consisting of fluorescent compounds, bioluminescent compounds, chemiluminescent compounds, radioisotopes, markers which can be detected by colorimetric methods, metal chelates, enzymes, biotin, streptavidin and magnet beads.

Generally preferred are markers which allow a direct detection, i.e. markers which can be detected without the need for specifically transporting the substrate having the surface under consideration to a detection device. In particular, markers are preferred which can be detected in-line during a production or coating process. The advantage of using a directly detectable marker is that it allows a direct quality control detection of samples on the production line. Samples do not have to be removed from the line to be characterized by sophisticated detection techniques, such as spectroscopic techniques. For example, detection can be done on-line by simply dipping the substrate into a solution of a marker labelled inorganic-peptide and subsequent observation of the signal provided by the marker, preferably a fluorescent marker, by eye, by microscopic analyses or with a camera so that it is immediately apparent whether the substrate has defects, or whether a coating is homogenous and has a good surface covering. Detection via a directly detectable marker is particularly convenient, e.g., for continuous production or coating processes.

In a preferred embodiment of the method of the invention, the detectable marker is a fluorescent compound, in particular a fluorescent dye. A fluorescent compound in accordance with the present invention includes compounds which emit light of a particular wavelength when exposed to electromagnetic radiation of a shorter wavelength. Non-limiting examples of fluorescent compounds are fluorescein, naphthofluorescein, the various known versions of GFPs, Rhodamine, Texas Red®, Pacific Blue®, Oregon Green®, Alexa Fluor® Dy, Cy3 or Cy5.

As will be understood, the detectable marker should be attached to the inorganic-binding peptide before it is contacted with the surface. It is generally preferred for the methods of the invention, that the detectable marker is covalently bound to the inorganic binding peptide. Moreover, it is preferred to attach the marker, preferably via a covalent bond, to the N-terminus of the peptide. Methods for the attachment of markers to peptides are established in the art. For example, the amino group which is available at the N-terminus of the peptide may be used to form an amide bond with a suitably functionalized marker, or may react with an epoxy group of a suitably functionalized marker, etc.

Methods for contacting the surface with an inorganic-binding peptide are not limited. The peptide may be contact with the surface in the form of a solution, a dispersion or a powder, but solutions are preferably used, in particular aqueous solutions. Contacting the surface with an inorganic-binding peptide may include applying a peptide to the surface, e.g. by spraying, rinsing or application by a brush, or may include immersing, e.g. dipping, the surface in a solution containing an inorganic peptide.

It should be understood that reference to aqueous environments, aqueous media, aqueous solutions or the like in this application, means solvent systems wherein 50% (v/v) or more, preferably 70% or more, more preferably 90% or more and in particular substantially 100% of the total volume of solvent(s) is water. Aqueous solutions containing inorganic binding peptides or used to wash surfaces to which inorganic binding peptides are bound may further comprise buffers and salts as needed.

It is to be noted that the methods of the invention are not limited to the application of single types of inorganic-binding peptides to a surface. Rather, methods are specifically envisaged wherein the surface is contacted parallelly or subsequently, with more than one, such as two, three or four types of inorganic-binding peptides which bind to different inorganic entities of interest. For example, this allows the parallel detection of different types of impurities on or within a surface. If plural types of inorganic-binding peptides are used, the detectable markers attached to the plural types of inorganic-binding peptides may be identical. Also encompassed by the methods of the present invention is the use of a plurality, such as for example two, three or four inorganic-binding peptides, each of which comprise a different detectable marker, such as for example fluorescent labels having different emission wavelengths, the use of such a plurality of differently labelled inorganic-binding peptides is particularly useful in the quality control of microstructured surfaces, such as electrical circuits, coated nano-objects etc.

Binding of the inorganic-binding peptide to inorganic entities of interest in or on the surface usually occurs spontaneously, without the need of applying external energy. For example, in order to achieve binding the peptide or peptide solution may remain in contact with the surface at a temperature ranging from above 0° C. to below 40° C., typically at or around room temperature, i.e. 20° C. over a period of seconds to several hours. Typically, contact times of 5 seconds or more, preferably 15 seconds or more and 1 hour or less are applied.

The removal of the unbound inorganic-binding peptide from the surface may be achieved by physically removing the peptide, e.g. withdrawing the surface from a solution of the peptide, washing unbound peptide or peptide solution from the surface, wiping unbound peptide or peptide solution off the surface, etc., or combinations of the above methods, such as withdrawing the surface from a solution of the peptide, followed by washing. Washing includes rinsing the surface with water or aqueous solutions or immersing the surface in water or aqueous solutions which may include buffers, where needed, and which often have a pH of 5 to 8, preferably 6 to 8.

The detection method used to detect the peptide remaining on the surface is of course appropriately selected depending on the type of marker used, i.e. a method should be used which is able to receive signals, radiation etc. emitted by the marker, or to excite the marker such that it emits signals, radiation, etc., and, where necessary, to transform the signal, radiation, etc., into a suitable form which can be perceived by humans or by an automated system. For example, if a fluorescent marker is used, detection can be carried out, e.g., by fluorescent imaging using a camera, visual inspection under an appropriate lamp, microscopic analysis etc. Preferred for the detection are methods or systems which can be applied in-line in a production or coating process.

The peptides adhering to inorganic entities of interest usually form a thin layer or film on the surface. Such films may be less than 10 nm, often even less than 1 nm thick, and are thus typically transparent for the eye. They do not compromise any further use of the substrate. If desired, the bound inorganic binding peptides can nevertheless be removed from the surface, e.g. by washing with an acidic or basic aqueous solution, e.g. at a pH ranging from 0 to 2 or at pH ranging from 12 to 14, by heating or by sonication. Thus, the methods of the invention are non-destructive for the surface to be analyzed.

As will be understood from the teachings above, inorganic-binding peptides can be used as quality control tools for defect detection on inorganic surfaces of any shapes. Due to high specificity, inorganic-binding peptides, which may be isolated by phage display and may be linked to a fluorescent dye are able to detect chemical composition defects of µm size by a simple microscopic analysis under fluorescence. This property has been validated, inter alia on galvanized steel substrates with a ZnO inorganic-binding peptide as well as on stainless steel and an amorphous $TiO_2$, e.g. as applied in plasma vapour deposition coating. Stainless steel is an important component finding many applications in surface coating. $TiO_2$ is a semiconductor and photocatalytic material whose applications can mainly be found in the biomedical, environmental or cosmetics domains. This system can be extended to any type of inorganic substrate using phage display technology. Once a sequence is identified, a peptide can be chemically synthesized and linked to a marker. A surface of interest can then be dipped into a peptide solution and observed under fluorescence.

The method of the invention process is able to identify chemical composition defects at the macroscopic and microscopic scale. Big defects can be visualized by eye under a simple fluorescent lamp whereas smaller defects could be detected by microscopic analyses under fluorescence. At that stage, the detection limit for the defect size is the detection limit of the microscope. Moreover, the detection limit could be decreased by using radioactive markers.

In accordance with the present invention, samples can be characterized continuously on the production line; they do not have to be removed from the line to be characterized by sophisticated spectroscopic techniques. It is a nondestructive technique, the peptide layer can be less than 1 nm thick and totally invisible to the naked eye and can be removed, e.g, by acidic treatment. By consequence, this process can find numerous applications in various domains where the quality of the surface in terms of composition, coating homogeneity, etc, is a priority (microelectronics, nanosensors, automobile painting, etc.).

Another advantage of the process is that it allows working without phages in order to avoid widespread dispersion of phages. Additionally, this process allows analysis of a high scale application in an industrial context.

A specific embodiment of the first aspect of the invention embodiment of the invention includes using a labelled inorganic-binding peptide for quality control detection on inorganic surfaces. The interaction between a ZnO-binding peptide VRTRDDARTHRK (SEQ ID NO:16) and a galvanized steel surface can be visualized with a fluorescent dye attached to the N-terminal end of a peptide. Galvanized steel surfaces are covered with a thin zinc oxide layer on their surface protecting them from corrosion. An interaction of a binding peptide with an inorganic surface can be visualized with a fluorescent profile depending on an intrinsic quality (in terms of chemical composition homogeneity) of a galvanized steel surface as well as of a surface pre-treatment. A fluorescent ZnO-binding peptide may be used to check the quality of galvanized steel's surface. The ZnO-binding peptide labelled with fluorescein allows an easy and in-line visualisation of galvanized steel surface intrinsic quality as well as quality of a surface pre-treatment (precoating), a critical point in siderurgy. In practice, samples do not have to be removed from a production line to be characterized by sophisticated spectroscopic techniques. Detection can be done on-line by simply dipping a substrate into a fluorescent inorganic-peptide solution and subsequent observation with a camera. It is non-destructive and the deposited peptide layer is typically less than 1 nm thick and totally transparent.

"Quality" of a surface not only concerns chemical composition homogeneity but also precise particle size, specified particle shape, etc. As such, inorganic binding peptides can be used in another field of growing interest: powder, especially nanopowder synthesis and more precisely the sorting of powders or nanopowders, i.e. the identification and/or isolation of powder particles having specified characteristics. Nanopowders are synthesised worldwide but the difficulty remains to produce nanopowder with the requested/expected monodisperse size, morphology and crystallinity (crystalline form). All these physical parameters are crucial to ensure peculiar properties like piezoelectricity, conductivity, etc. Until now, the fabrication process is often adapted in order to obtain nanopowders with monodisperse size distribution. Techniques like Catalytic Chemical Vapor Deposition, Chemical Precipitation/Coprecipitation, Electro-Explosion, and Plasma Enhanced Chemical Vapor Deposition are used in that aim by many companies of nanopowder syntheses. To further refine the segregation, physical processes like size selective precipitation, circulation into a gas stream and further setting, high performance liquid chromatography, gel electrophoresis, interaction with/displacement in an electrostatic field, centrifugation at increasing rotational speed, light scattering, phase transition between aqueous/organic phases (capped nanoparticles), ultrasonic separation or acoustic streaming, are performed after nanopowder synthesis in order to select the particle size of interest.

Thus, in a second aspect of the invention, inorganic-binding peptides can be used as tools for the isolation of powder particles, and in particular for nanopowder sorting, by chemical composition, morphology and also on the basis of their crystallographic forms.

According to this second aspect, the invention thus provides a method for the isolation of powder particles comprising an inorganic entity of interest from a mixture of powder particles, comprising the steps of:

(a) contacting the powder with an inorganic-binding peptide capable of specifically binding to the inorganic entity of interest, and (b) isolating the powder particles to which the inorganic binding peptide has bound.

The powders which can be subjected to the method of this embodiment typically include powder particles comprising or consisting of inorganic materials (in the following, the powder particles comprising or consisting of inorganic materials will be referred to as inorganic powder particles). It will be understood that the method is suitable both for isolating inorganic powder particles from purely inorganic powder mixtures, or from mixtures containing both inorganic powder particles and other types, especially powder particles consisting of organic, e.g. polymeric materials.

The method according to the second aspect of the invention may be applied to powder particles of various sizes, including those with a size, e.g. as measured by sieving methods, of less than 1 mm, particularly less than 100 μm, or less than 10 μm, and even more preferred less than 1 μm. The method is particularly suitable for nanopowders. Such powders preferably have a particle size, frequently expressed as the average particle size, of 500 nm or less, preferably 300 nm or less and 10 nm or more, preferably 50 nm or more. Often, the particle is size ranges around 250 to 100 nm. Such particles sizes can be measured by granulometric methods known in the art, e.g. laser diffractometry.

The powders subjected to the method of this second aspect are preferably non-soluble in water. Typically, their solubility is lower than 100 mg/l, more preferably lower than 10 mg/l or even less than 1 mg/l in water at a temperature of 20° C.

As indicated above, reference to the "isolation of powder particles" includes methods wherein powder particles comprising an inorganic entity of interest are identified in and separated from particles not comprising the inorganic entity of interest in a powder mixture, or wherein they are directly separated from the particles not comprising the inorganic entity of interest. This identification and/or separation is also referred to herein as the sorting of powders, especially nanopowders.

The "inorganic entity of interest" which is comprised in or provided by the powder particles to be isolated according to the method of the invention includes an inorganic compound which is characterized by its chemical composition, e.g. a metal, metal oxide or a semiconductor or carbon. Suitable compounds include those selected from aluminium, antimony, beryllium, cadmium, copper, chrome, gold, iron, lead, selenium, palladium, platinum, titanium, zinc and oxides thereof, particularly from $TiO_2$, $ZnO$, $Al_2O_3$ or from steel, inclusive of stainless steel. For example, the powder particles to be isolated may consist of the materials mentioned above to which the inorganic binding peptide can specifically bind. In another embodiment of the second aspect of the invention, the inorganic entity may also be a specific inorganic crystallographic form of the particle or in the particle to be isolated, e.g. crystalline, amorphous, or a specific crystal form. In yet another embodiment, the inorganic entity of interest is an inorganic powder particle itself, which has a specific diameter to which the inorganic-binding peptide will selectively bind. Other particle morphologies apart from the particle size can also be envisaged as a criterion for the isolation of powder particles.

It will be understood that the inorganic entities of interest are typically entities which can be found at or near the surface of the powder particles, preferably at the surface.

Powder mixtures to be subjected to the method according to the invention typically comprise a least two types of powders, one type providing the inorganic entity of interest, the other one not providing the inorganic entity of interest. However, the number of types of powders is not particularly limited, such as in the case of powder mixtures containing inorganic particles over a range of sizes from which powder particles of a specific particle size are to be isolated.

The powder mixture may be subjected to the method as such, but it is preferred to disperse the powder particles to provide a suspension, preferably an aqueous suspension, of the powder mixture on which the method according to the invention is to be performed. It should be understood that reference to an aqueous suspension, aqueous media, aqueous solutions or the like in this application, means solvent systems wherein 50% (v/v) or more, preferably 70% or more, more preferably 90% or more and in particular substantially 100% of the total volume of solvent(s) is water. Aqueous solutions containing inorganic binding peptides or used to wash particles to which inorganic binding peptides are bound may further comprise buffers and salts as needed.

Binding of the inorganic-binding peptide to inorganic entities of interest usually occurs spontaneously, without the need of applying external energy. For example, in order to achieve a binding the peptide/peptide solution may remain in contact with the powder particles at a temperature ranging from above 0° C. to below 40° C., typically at or around room temperature, i.e. 20° C. over a period of seconds to several hours. Typically, contact times of 5 seconds or more, preferably 15 seconds or more and 1 hour or less are applied.

In one preferred embodiment, the method for the isolation of powder particles using an inorganic-binding peptide includes a step wherein the inorganic-binding peptide is attached to a solid support. The support is not particularly limited in its shape or with respect to the material used. For example, resins of any composition and form, including resin beads and beads with a magnetic core, fibers, tubes, fabrics or membranes can be envisaged. The support should have a size which allows its convenient handling such that the inorganic-binding peptides bound to the powder particles of interest can be separated together with the support to which they are attached from the remaining particles of the powder.

In this context, according to one strategy which is available, the inorganic-binding peptide is first contacted with the powder mixture to bind to the powder particles comprising or providing the inorganic entity of interest, and subsequently the complex (inorganic-binding peptide)-particle is attached to a support, preferably via its N-terminus, so that it can be conveniently separated from the other powder particles.

Following this strategy, as schematically shown in FIG. 11 for a mixture of particles X comprising or providing an inorganic entity of interest and particles Y not comprising the entity of interest, the inorganic-binding peptide specifically binding to X can be added to a suspension of a blend of particles X and Y to be sorted (FIG. 11A). The inorganic-binding peptide will bind specifically onto particles X. In a first example (FIG. 11A1), the suspension of particles Y and the complexes (inorganic-binding peptide)-particle can be further attached to a support displaying a great affinity for the inorganic-binding peptide or even more generally for amino acid-based molecules. As a result, particles Y will stay in suspension and the complex (inorganic-binding peptide)-particle X can be retrieved from the suspension together with the affinity support. In a second example, the inorganic binding peptide comprises a tag, e.g. a histidine tag or any other chemical or biological moiety allowing for further affinity binding to an adequate complementary support; examples are biotinstreptavidin like systems or histidine-metal ions like systems. In still another example, the inorganic binding peptide can be grafted with a superhydrophobic l-hydrophilic chemical or biological adduct and the sorting could be processed based on this newly induced physicochemical specific characteristic of the complex [particle X-inorganic binding peptide-adduct].

An alternative strategy includes the attachment of the inorganic-binding peptide to a support before it is contacted with the powder or the powder suspension. Afterwards the support with the inorganic-binding peptide attached to it is contacted with the powder or powder suspension. According to this embodiment, a support to which the inorganic-binding peptide is attached is contacted with the powder to allow the powder particles comprising or providing the inorganic entity of interest to bind to the inorganic-binding peptide, such that the inorganic-binding peptide acts as a linker between the particles and the support. In order to isolate the particles of interest, the support can be contacted with and subsequently removed from the powder mixture, or the powder mixture, especially in the form of a suspension, can pass along or through the support such that the particles of interest are captured by the inorganic-binding peptide. The support can be organic, inorganic or biological in nature. In a preferred embodiment, the inorganic binding peptide can be attached at its N-terminus to the support. It is also preferred that the attachment is achieved via a covalent bond, such as an ester or amide bond, formed between the surface of the support and the inorganic-binding peptide.

For example, as schematically shown in FIG. 11 for a mixture of particles X comprising or providing an inorganic entity of interest and particles Y not comprising the entity of interest (cf. FIG. 11B), the inorganic binding peptide can be grafted onto a macroporous material framework (cf. FIG. 11B2); the suspension of particles, in particular nanoparticles to be sorted can be contacted or sieved with the functionalised framework, particles X instantly bind to the inorganic-binding peptide and particles Y flow through. In an alternate example (FIG. 11B1) the inorganic-binding peptide can be attached to a matrix, like beads for chromatography or on a resin or on a membrane of any type of chemical composition and any physical form; consequently the suspension of nanoparticles to be sorted is contacted with, e.g. filtered or sieved onto the functionalised matrix, resin, membrane (tangential filtration for example), particles X instantly bind to the inorganic-binding peptide and particles Y flow through. The functionalized framework or matrix can also be ceramic tubes or any other. It is a particular advantage of this method according to the invention that functionalized matrices can be re-used several times, such as two or more or even three or more times, after the particles of interest have been separated to complete their isolation.

In a preferred embodiment of the strategy using a solid matrix to which the inorganic-binding peptide is attached before it is contacted with the powder particles, a matrix is used which comprises or consists of magnetic beads. For example, magnetic beads are available wherein a magnetic core is covered by a functionalized sheath onto which the inorganic-binding peptide can be grafted. For example, the inorganic binding peptide can be grafted on magnetic beads bearing epoxy groups. After binding of the inorganic-binding peptide to powder particles, in particular nanoparticles, the magnetic beads can be retrieved by magnetisation of the particle blend suspension.

In order to complete the isolation or the separation of the powder particles comprising or providing an inorganic entity of interest from a powder mixture, it is usually beneficial to cleave the bond between the inorganic-binding peptide and the particles once the particles not comprising the inorganic entities have been removed. The cleavage of the bond can be achieved, e.g. via a treatment in an acidic or basic aqueous solution with a pH typically ranging from 0 to 2 or from 12 to 14, or by sonication. This may include immersing the support in an aqueous solution, or spraying the aqueous solution onto the support. Subsequently, the particles of interest can be conveniently retrieved.

The method according to the second aspect of the invention may comprise optional additional washing steps, e.g. in order to effectively remove particles not comprising providing the inorganic entity of interest from a support to which the particles of interest are bound via the inorganic-binding peptide. Such additional washing steps can be carried out using conditions well known, e.g. using buffer solutions at a pH of around 5 to 8, preferably 6 to 8 or on the basis of the teachings of the examples provided below, optionally in conjunction with the teachings of the documents cited therein.

As will be understood from the above, the method according to this second aspect of the invention uses inorganic-binding peptides as tools/probe/sensor for nanopowder sorting in function of the size, morphology and crystallographic state. Inorganic binding peptides are able to pick up in a powder mixture, the powder with the good/target chemical composition, morphology and crystallographic forms. Inorganic binding peptides have for example been shown to be able to recognize one crystallographic form in a mixture of Au polycrystalline powder. If linked to a magnetic bead, inorganic binding peptides may be good tools for selecting and isolating a specific form of nanopowder in a nanopowder mixture by simple magnetic isolation. This can lead to a technological breakthrough to a wide array of applications in numerous sectors (pharmacy, aeronautic, construction, automobile, medical, etc.) where using a monodisperse nanopowder is fundamental.

In another preferred embodiment of the method of the invention the inorganic-binding peptide is selected by phage display, bacterial or yeast cell display or in vitro display.

The term "phage display" has been described herein in more detail.

The term "bacterial or yeast cell display", in accordance with the present invention, refers to display technologies in which libraries of polypeptides are displayed on the surface of bacteria or yeast cells (biopanning).

The term "in vitro display", in accordance with the present invention, subsumes all in vitro display technologies based on the exposition of a library of peptides on surfaces, such as for example the surface of a phage, a bacteria, a yeast cell.

The invention provides methods for generating and isolating novel inorganic-binding peptides that preferably have a high affinity for a selected inorganic material. One known route for the isolation of inorganic-binding polypeptides is to use combinatorial biology techniques described in the application WO03/078451 which mainly relies on the use of the phage display technology. A large random library of peptides of identical lengths but different amino acid composition is used to mine specific sequences that strongly bind to a chosen inorganic surface. Each phage produces and displays a different random peptide. At this stage, a heterogeneous mixture of recombinant phages is put in contact with the inorganic substrate. Several washing cycles of the phages eliminate non-specific binders by disrupting weak interactions with the substrate. Bound phages are then eluted from the surfaces and amplified in bacteria. Several inorganic-binding peptides have already been identified by phage display or cell surface display against inorganic powders and a few against flat surfaces like gold, aluminum or polypyrrol surfaces. Some of them are listed in Table 1.

| Materials | State | Sequence |
|---|---|---|
| Au(111) | Flat surface | MHGKTQATSGTIQS (SEQ ID NO: 1) |
| Au (001) | | SKTSLGQSGASLQGSEKLTNG (SEQ ID NO: 2); (e.g. Brown 1997) |
| Pt | powder | DRTSTWR (SEQ ID NO: 3) QSVTSTK (SEQ ID NO: 4) (e.g. Oren 2005) |
| Pd | powder | SVTQNKY (SEQ ID NO: 5) SPHPGPY (SEQ ID NO: 6) (e.g. Jószai 2006) |
| Al | Flat surface | VPSSGPQDTGTT (SEQ ID NO: 7) (e.g. Zuo 2005) |
| Ag | powder | AYSSGAPPMPPF (SEQ ID NO: 8) NPSSLFRYLPSD (SEQ ID NO: 9) (e.g. Naik 2002 or Xu 2005) |
| SiO2 | Amorphous powder | MSPHPHPRHHHT (SEQ ID NO: 10) RGRRRRLSCRLL (SEQ ID NO: 11) KPSHHHHHTGAN (SEQ ID NO: 12) (e.g. Naik 2002) |
| zeolites | powder | VKTQATSREEPPRLPSKHRPG (SEQ ID NO: 13) MDHGKYRQKGATPG (SEQ ID NO: 14) (e.g. Schembri 1999) |
| ZnO | powder | NTRMTARQHANHKSTQ (SEQ ID NO: 15) VRTRDDARTHRK (SEQ ID NO: 16) (e.g. Kjaergaard 2000) |
| CaCO3 | Calcite or aragonite cristal powder | HTQNMRMYEPWF (SEQ ID NO: 17) DVFSSFNLKHMR (SEQ ID NO: 18) (e.g. Gaskin 2000) |
| Cr2O3 | Cristal powder | VVRPKAATN (SEQ ID NO: 19) RIRHRLVGQ (SEQ ID NO: 20) (e.g. Gaskin, 2004) |
| Ti | powder | RKLPDAPGMHTW (SEQ ID NO: 21) (e.g. Sano 2003) |
| TiO2 | Anatase powder | CHKKPSKSC (SEQ ID NO: 22) (e.g. Chen 2006) |
| Fe2O3 | powder | RRTVKHHVN (SEQ ID NO: 23) (e.g. Brown 1997) |
| GaAs | Monocristal powder | AQNPSDDNNTHTH (SEQ ID NO: 24) RLELAIPLQGSG (SEQ ID NO: 25) TPPRPIQYNHTS (SEQ ID NO: 26) (e.g. Whaley 2000) |
| ZnS, CdS | Nanocristal powder | NNPMHQN (SEQ ID NO: 27) (e.g. Lee 2002 or Mao 2004) |
| C nanotube | C nanotube | HWSAWWIRSNQS (SEQ ID NO: 28) (e.g. Wang 2003) |
| PPyCl | Flat surface | THRTSTLDYFVI (SEQ ID NO: 29) (e.g. Sanghvi 2005) |

Table 1: Inorganic peptides identified by phage display or cell surface display against inorganic powders or against flat surfaces.

In accordance with the above, the inventions further provides as a third aspect a method for the identification of defects or inhomogenieties on a surface by detecting an inorganic entity of interest, comprising the steps of:

(a1)) selecting a peptide against the inorganic entity of interest by display technologies which is capable of specifically binding to the inorganic entity of interest;

(a2) synthesizing or expressing the inorganic-binding peptide selected in (a1) followed by the steps of:

(a) contacting the surface with the inorganic-binding peptide, which carries a detectable marker and is capable of specifically binding to the inorganic entity of interest;

(b) removing unbound peptide; and (c) detecting the peptide remaining on the surface.

It will be understood that the embodiments and preferred embodiments of this method are the same as those disclosed for the method for the identification of defects or inhomogenieties on a surface according to the first aspect of the invention. It will be understood that the detectable marker is generally attached to the peptide after step (a2) and before step (a) or, alternatively, is expressed together with the peptide in step (a2).

Similarly, the invention provides as a fourth aspect a method for the isolation of powder particles comprising an inorganic entity of interest from a mixture of powder particles, comprising the steps of:

(a1) selecting a peptide against the inorganic entity of interest by display technologies which is capable of specifically binding to the inorganic entity of interest;

(a2) synthesizing or expressing the inorganic-binding peptide selected in (a1) followed by the steps of:

(a) contacting the powder with the inorganic-binding peptide capable of specifically binding to the inorganic entity of interest; and (b) isolating the powder particles to which the inorganic binding peptide has bound.

It will be understood that the embodiments and preferred embodiments of this method are the same as those disclosed for the method for the isolation of powder particle according to the second aspect of the invention.

In a preferred embodiment, the synthesis of the peptide in step (a2) is a chemical synthesis. Methods for the chemical synthesis of a peptide are well known in the art and include the methods recited elsewhere herein.

In a preferred embodiment, the expression of the peptide in step (a2) is a molecular biological method of expressing the peptide. Molecular biology means, e.g. recombinant methods, for expressing a peptide are well known in the art and include the methods recited elsewhere herein.

In a preferred embodiment, the attachment of the synthesized peptide to a marker is a covalent attachment.

The present invention further relates to an inorganic-binding peptide comprising the amino acid sequence MTWDPSLASPRS (SEQ ID NO: 31). The present invention further relates to an inorganic-binding peptide comprising the amino acid sequence LNAAVPFTMAGS (SEQ ID NO: 32).

Said peptides includes, but are not limited to, peptides consisting of the respective sequence as well as peptides having the respective sequence and having additional amino acid residues at either the N-terminus, the C-terminus or at both ends, preferably while essentially retaining their binding specificity. Such additional amino acid residues, also referred to as flanking regions, at the termini of the peptide of the invention are preferably at least one amino acid residue, more preferably at least two amino acid residues, more preferably at least three amino acid residues and even more preferably at least four amino acid residues, such as at least five, six or seven amino acid residues.

Thus, the present invention provides novel inorganic-binding peptides. Novel inorganic-binding peptides of the invention include the stainless steel binding peptide MTWDPSLASPRS (SEQ ID NO: 31) and the $TiO_2$ binding peptide LNAAVPFTMAGS (SEQ ID NO: 32).

In another embodiment, the present invention relates to a nucleic acid molecule encoding a peptide of the invention.

In a preferred embodiment, the nucleic acid molecule is DNA.

It will be readily appreciated by the skilled person that more than one nucleic acid may encode a peptide of the present invention due to the degeneracy of the genetic code. Degeneracy results because a triplet code designates 20 amino acids and a stop codon. Because four bases exist which are utilized to encode genetic information, triplet codons are required to produce at least 21 different codes. The possible $4^3$ possibilities for bases in triplets give 64 possible codons, meaning that some degeneracy must exist. As a result, some amino acids are encoded by more than one triplet, i.e. by up to six. The degeneracy mostly arises from alterations in the third position in a triplet. This means that nucleic acid molecules having different sequences, but still encoding the same polypeptide lie within the scope of the present invention.

Further, the invention relates to a vector comprising the nucleic acid molecule of the invention.

Preferably, the vector is a plasmid, cosmid, virus, bacteriophage or another vector used conventionally e.g. in genetic engineering. Preferably, the vector is an expression vector. An expression vector according to this invention is capable of directing the replication, and the expression of the nucleic acid molecule of the invention and the peptide, fusion peptide or fusion polypeptide encoded thereby. Suitable expression vector are for example described below in the context of expressing an inorganic binding peptide fusion protein expressed on the surface of a phage or cell.

The nucleic acid molecule of the present invention may be inserted into several commercially available vectors. Non-limiting examples include prokaryotic plasmid vectors, such as the pUC-series, pBluescript (Stratagene), the pET-series of expression vectors (Novagen) or pCRTOPO (Invitrogen), lambda gt11, pJOE, the pBBR1-MCS series, pJB861, pBSMuL, pBC2, pUCPKS, pTACT1 and vectors compatible with expression in mammalian cells like pREP (Invitrogen), pCEP4 (Invitrogen), pMC1neo (Stratagene), pXT1 (Stratagene), pSG5 (Stratagene), EBO-pSV2neo, pBPV-1, pdBPVMMTneo, pRSVgpt, pRSVneo, pSV2-dhfr, pIZD35, Okayama-Berg cDNA expression vector pcDV1 (Pharmacia), pRc/CMV, pcDNA1, pcDNA3 (Invitrogene), pSPORT1 (GIBCO BRL), pGEMHE (Promega), pLXIN, pSIR (Clontech), pIRES-EGFP (Clontech), pEAK-10 (Edge Biosystems) pTriEx-Hygro (Novagen) and pCINeo (Promega). Examples for plasmid vectors suitable for *Pichia pastoris* comprise e.g. the plasmids pAO815, pPIC9K and pPIC3.5K (all Invitrogen).

One aspect of the invention includes a replicable expression vector comprising a nucleic acid sequence encoding an inorganic-binding peptide, wherein the gene fusion encodes a fusion protein comprising an inorganic-binding peptide fused to all or a portion of a viral coat protein. Also included is a library of diverse replicable expression vectors comprising a plurality of gene fusions encoding a plurality of different fusion proteins including a plurality of the inorganic-binding peptide as described above. The vectors can include a variety of components and are preferably constructed to allow for movement of antibody variable domain between different vectors and/or to provide for display of the fusion proteins in different formats.

Examples of vectors include phage vectors. The phage vector has a phage origin of replication allowing phage replication and phage particle formation. The phage is preferably a filamentous bacteriophage, such as an M13, f1, fd, Pf3 phage or a derivative thereof, or a lambdoid phage, such as lambda, 21, phi80, phi81, 82, 424, 434, etc., or a derivative thereof.

Examples of viral coat proteins include infectivity protein PIII, major coat protein PVIII, p3, Soc (T4), Hoc (T4), gpD (of bacteriophage lambda), minor bacteriophage coat protein 6 (pVI) (filamentous phage; *J Immunol Methods*. 1999 Dec. 10; 231(1-2):39-51), variants of the M13 bacteriophage major coat protein (P8) (*Protein Sci* 2000 April; 9(4):647-54). The fusion protein can be displayed on the surface of a phage and suitable phage systems include M13K07 helper phage, M13R408, M13-VCS, and Phi X 174, pJuFo phage system (*J Virol*. 2001 August; 75(15):7107-13.v), hyperphage (*Nat Biotechnol*. 2001 January; 19(1):75-8). A preferred helper phage is M13K07, and a preferred coat protein is the M13 Phage gene III coat protein. The preferred host is *E. coli*, and protease deficient strains of *E. coli*. Vectors, such as the fth1 vector (*Nucleic Acids Res*. 2001 May 15; 29(10):E50-0) can be useful for expression of a fusion protein.

The expression vector also can have a secretory signal sequence fused to the DNA encoding each subunit of the antibody or fragment thereof. This sequence is typically located immediately 5' to the gene encoding the fusion protein, and will thus be transcribed at the amino terminus of the fusion protein. However, in certain cases, the signal sequence has been demonstrated to be located at positions other than 5' to the gene encoding the protein to be secreted. This sequence targets the protein to which it is attached across the inner membrane of the bacterial cell. The DNA encoding the signal sequence may be obtained as a restriction endonuclease fragment from any gene encoding a protein that has a signal sequence. Suitable prokaryotic signal sequences may be obtained from genes encoding, for example, LamB or OmpF (Wong et al., Gene, 68:1931 (1983), MalE, PhoA and other genes. A preferred prokaryotic signal sequence for practicing this invention is the *E. coli* heat-stable enterotoxin II (STII) signal sequence as described by Chang et al., Gene 55:189 (1987), and malE.

The vector also typically includes a promoter to drive expression of the fusion protein. Promoters most commonly used in prokaryotic vectors include the lac Z promoter system, the alkaline phosphatase pho A promoter (Ap), the bacteriophage λpL promoter (a temperature sensitive promoter), the tac promoter (a hybrid trp-lac promoter that is regulated by the lac repressor), the tryptophan promoter, and the bacteriophage T7 promoter. For general descriptions of promoters, see section 17 of Sambrook et al. supra. While these are the most commonly used promoters, other suitable microbial promoters may be used as well.

The vector can also include other nucleic acid sequences, for example, sequences encoding gD tags, c-Myc epitopes, poly-histidine tags, fluorescence proteins (eg., GFP), or betagalactosidase protein which can be useful for detection or purification of the fusion protein expressed on the surface of the phage or cell. Nucleic acid sequences encoding, for example, a gD tag, also provide for positive or negative selection of cells or virus expressing the fusion protein. In some embodiments, the gD tag is preferably fused to an antibody variable domain which is not fused to the viral coat protein component. Nucleic acid sequences encoding, for example, a polyhistidine tag, are useful for identifying fusion proteins including antibody variable domains that bind to a specific antigen using immunohistochemistry. Tags useful for detection of antigen binding can be fused to either an antibody variable domain not fused to a viral coat protein component or an antibody variable domain fused to a viral coat protein component.

Another useful component of the vectors used to practice this invention is phenotypic selection genes. Typical phenotypic selection genes are those encoding proteins that confer antibiotic resistance upon the host cell. By way of illustration, the ampicillin resistance gene (amp'), and the tetracycline resistance gene (tet') are readily employed for this purpose.

The invention furthermore refers to a host cell comprising the nucleic acid molecule or the vector of the invention.

Vectors constructed as described in accordance with the invention are introduced into a host cell for amplification and/or expression. Vectors can be introduced into host cells using standard transformation methods including electroporation, calcium phosphate precipitation and the like. If the vector is an infectious particle such as a virus, the vector itself provides for entry into the host cell. Transfection of host cells containing a replicable expression vector which encodes the gene fusion and production of phage particles according to standard procedures provides phage particles in which the fusion protein is displayed on the surface of the phage particle. Preferred host cells include, without being limiting, *E. coli*.

In a different embodiment, the invention relates to a method for producing a peptide of the invention, comprising culturing the host of the invention under suitable conditions and isolating the peptide produced. Suitable methods to produce peptides in appropriate hosts are known in the art and have been described above. In addition, a peptide of the invention can also be produced by in vitro translation of mRNA in a suitable cell-free expression system or can be synthesized as described above.

In a preferred embodiment of the method of the invention, the inorganic surface structure of interest is stainless steel and the inorganic-binding peptide specifically binding to said inorganic structure of interest is the peptide of the invention comprising the amino acid sequence MTWDPSLASPRS (SEQ ID NO: 31).

In another preferred embodiment of the method of the invention, the inorganic surface structure of interest is $TiO_2$ and inorganic-binding peptide specifically binding to said inorganic structure of interest is the peptide of the invention comprising the amino acid sequence LNAAVPFTMAGS (SEQ ID NO: 32).

GENERAL DEFINITIONS

Amino acids are represented herein as either a single letter code or as the three letter code or both. These codes are well known in the art. For example, the codes for the standard amino acids are as shown in table 2 below.

TABLE 2 single letter and three letter codes for standard amino acids

| Amino Acid | single letter code | three letter code |
|---|---|---|
| Alanine | A | Ala |
| Arginine | R | Arg |
| Asparagine | N | Asn |
| Aspartic acid | D | Asp |

TABLE 2-continued single letter and three letter codes for standard amino acids

| Amino Acid | single letter code | three letter code |
|---|---|---|
| Cysteine | C | Cys |
| Glutamic acid | E | Glu |
| Glutamine | Q | Gln |
| Glycine | G | Gly |
| Histidine | H | His |
| Isoleucine | I | Ile |
| Leucine | L | Leu |
| Lysine | K | Lys |
| Methionine | M | Met |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |

The term "affinity purification", as used herein, means the purification of a molecule based on a specific attraction or binding of the molecule to a chemical or binding partner to form a combination or complex which allows the molecule to be separated from impurities while remaining bound or attracted to the partner moiety.

As used herein, "codon set" refers to a set of different nucleotide triplet sequences used to encode desired variant amino acids. A set of oligonucleotides can be synthesized, for example, by solid phase synthesis, including sequences that represent all possible combinations of nucleotide triplets provided by the codon set and that will encode the desired group of amino acids. A standard form of codon designation is that of the IUB code, which is known in the art and described herein.

"Cell", "cell line", and "cell culture" are used interchangeably herein and such designations include all progeny of a cell or cell line. Thus, for example, terms like "transformants" and "transformed cells" include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

As used herein, the term "control sequences" when referring to expression means DNA sequences necessary for the expression of an operably linked coding sequence in a particular host organism. The control sequences that are suitable for prokaryotes, for example, include a promoter, optionally an operator sequence, a ribosome binding site, and possibly, other as yet poorly understood sequences. Eukaryotic cells are known to utilize promoters, polyadenylation signals, and enhancers The term "coat protein", in accordance with the present invention, means a protein, at least a portion of which is present on the surface of the virus particle. From a functional perspective, a coat protein is any protein which associates with a virus particle during the viral assembly process in a host cell, and remains associated with the assembled virus until it infects another host cell. The coat protein may be the major coat protein or may be a minor coat protein. A "major" coat protein is generally a coat protein which is present in the viral coat at preferably at least about 5, more preferably at least about 7, even more preferably at least about 10 copies of the protein or more. A major coat protein may be present in tens, hundreds or even thousands of copies per virion. An example of a major coat protein is the p8 protein of filamentous phage.

As used herein the term "detection limit" for a chemical entity in a particular assay is the minimum concentration of that entity which can be detected above the background level for that assay. For example, in the phage ELISA, the "detection limit" for a particular phage displaying a particular inorganic-binding peptide is the phage concentration at which the particular phage produces an ELISA signal above that produced by a control phage not displaying the inorganic-binding peptide.

"Polypeptide", in accordance with the present invention, refers to a peptide or protein containing two or more amino acids linked by peptide bonds, and includes peptides, oligomers, proteins, and the like. The term "peptide" as used herein describes a group of molecules consisting of up to 30 amino acids, whereas "proteins" consist of more than 30 amino acids. Polypeptides can contain natural, modified, or synthetic amino acids. Polypeptides can also be modified naturally, such as by post-translational processing, or chemically, such as amidation acylation, cross-linking, and the like.

A "fusion protein" and a "fusion polypeptide" refers to a polypeptide having two portions covalently linked together, where each of the portions is a polypeptide having a different property. The property may be a biological property, such as activity in vitro or in vivo. The property may also be a simple chemical or physical property, such as binding to a target antigen, catalysis of a reaction, etc. The two portions may be linked directly by a single peptide bond or through a peptide linker containing one or more amino acid residues. Generally, the two portions and the linker will be in reading frame with each other. Preferably, the two portions of the polypeptide are obtained from heterologous or different polypeptides. An example of a fusion protein is an inorganic-binding peptide fused to a phage coat protein. Another example of a fusion protein is an inorganic-binding peptide fused to a marker peptide or protein.

A large number of suitable methods exist in the art to produce polypeptides in appropriate hosts. If the host is a unicellular organism such as a prokaryote, a mammalian or insect cell, the person skilled in the art can revert to a variety of culture conditions. Conveniently, the produced protein is harvested from the culture medium, lysates of the cultured organisms or from isolated (biological) membranes by established techniques. In the case of a multicellular organism, the host may be a cell which is part of or derived from a part of the organism, for example said host cell may be the harvestable part of a plant. A preferred method involves the recombinant production of protein in hosts as indicated above. For example, nucleic acid sequences comprising the nucleic acid molecule according to the invention can be synthesized by PCR and inserted into an expression vector. Subsequently a suitable host may be transformed with the expression vector. Thereafter, the host is cultured to produce the desired polypeptide, which is isolated and purified. Such methods are well known in the art (see, e.g., Sambrook et al., supra).

The expression vector also can have a secretory signal sequence fused to the DNA encoding the peptide. This sequence is typically located immediately 5' to the gene encoding the fusion protein, and will thus be transcribed at the amino terminus of the fusion protein. However, in certain cases, the signal sequence has been demonstrated to be located at positions other than 5' to the gene encoding the protein to be secreted. This sequence targets the protein to which it is attached across the inner membrane of the bacterial cell. The DNA encoding the signal sequence may be obtained as a restriction endonuclease fragment from any gene encoding a protein that has a signal sequence. Suitable prokaryotic signal sequences may be obtained from genes encoding, for example, LamB or OmpF (Wong et al., Gene, 68:1931 (1983), MalE, PhoA and other genes. A preferred prokaryotic signal sequence for practicing this invention is the E. coli heat-stable enterotoxin H (STH) signal sequence as described by Chang et al., Gene 55:189 (1987), and malE.

The vector also typically includes a promoter to drive expression of the fusion protein. Promoters most commonly used in prokaryotic vectors include the lac Z promoter system, the alkaline phosphatase phoA promoter (Ap), the bacteriophage λpL promoter (a temperature sensitive promoter), the tac promoter (a hybrid trp-lac promoter that is regulated by the lac repressor), the tryptophan promoter, and the bacteriophage T7 promoter. For general descriptions of promoters, see section 17 of Sambrook et al. supra. While these are the most commonly used promoters, other suitable microbial promoters may be used as well.

The vector can also include other nucleic acid sequences, for example, sequences encoding gD tags, c-Myc epitopes, poly-histidine tags, fluorescence proteins (eg., GFP), or betagalactosidase protein which can be useful for detection or purification of the fusion protein expressed on the surface of the phage or cell. Nucleic acid sequences encoding, for example, a gD tag, also provide for positive or negative selection of cells or virus expressing the fusion protein. In some embodiments, the gD tag is preferably fused to a peptide which is not fused to the viral coat protein component. Nucleic acid sequences encoding, for example, a polyhistidine tag, are useful for identifying fusion proteins including peptides that bind to a specific antigen using immunohistochemistry. Tags useful for detection of peptide binding can be fused to either a peptide not fused to a viral coat protein component or a peptide fused to a viral coat protein component.

An alternative method for producing a polypeptide is in vitro translation of mRNA. Suitable cell-free expression systems for use in accordance with the present invention include rabbit reticulocyte lysate, wheat germ extract, canine pancreatic microsomal membranes, E. coli S30 extract, and coupled transcription/translation systems such as the TNT-system (Promega). These systems allow the expression of recombinant polypeptides upon the addition of cloning vectors, DNA fragments, or RNA sequences containing coding regions and appropriate promoter elements.

In addition to recombinant production, the polypeptide or the fusion polypeptide of the invention may be produced synthetically, e.g. by direct peptide synthesis using solid-phase techniques (cf Stewart et al. (1969) Solid Phase Peptide Synthesis; Freeman Co, San Francisco; Merrifield, J. Am. Chem. Soc. 85 (1963), 2149-2154). Synthetic protein synthesis may be performed using manual techniques or by automation. Automated synthesis may be achieved, for example, using the Applied Biosystems 431 A Peptide Synthesizer (Perkin Elmer, Foster City Calif.) in accordance with the instructions provided by the manufacturer. Various fragments may be chemically synthesized separately and combined using chemical methods to produce the full length molecule. As indicated above, chemical synthesis, such as the solid phase procedure described by. Houghton (Proc. Natl. Acad. Sci., 1985, 82: 5131) can be used.

The term "nucleic acid molecule" as used interchangeably with the term "polynucleotide", in accordance with the present invention, includes DNA, such as cDNA or genomic DNA, and RNA. Further included are nucleic acid mimicking molecules known in the art such as synthetic or semi-synthetic derivatives of DNA or RNA and mixed polymers. Such nucleic acid mimicking molecules or nucleic acid derivatives according to the invention include phosphorothioate nucleic acid, phosphoramidate nucleic acid, 2'-O-methoxyethyl ribonucleic acid, morpholino nucleic acid, hexitol nucleic acid (HNA)), peptide nucleic acid (PNA) and locked nucleic acid (LNA) (see Braasch and Corey, Chem Biol 2001, 8: 1). LNA is an RNA derivative in which the ribose ring is constrained by a methylene linkage between the 2'-oxygen and the 4'-carbon. They may contain additional non-natural or derivative nucleotide bases, as will be readily appreciated by those skilled in the art.

"Heterologous DNA" is any DNA that is introduced into a host cell. The DNA may be derived from a variety of sources including genomic DNA, cDNA, synthetic DNA and fusions or combinations of these. The DNA may include DNA from the same cell or cell type as the host or recipient cell or DNA from a different cell type, for example, from a mammal or plant. Preferably, the DNA includes DNA from a different cell type. The DNA may, optionally, include marker or selection genes, for example, antibiotic resistance genes, temperature resistance genes, etc.

As used herein, "library" refers to a plurality of peptide or polypeptide sequences (for example, polypeptides of the invention), or the nucleic acids that encode these sequences.

"Ligation" is the process of forming phosphodiester bonds between two nucleic acid fragments. For ligation of the two fragments, the ends of the fragments must be compatible with each other.

"Oligonucleotides" are short-length, single- or double-stranded polydeoxynucleotides that are chemically synthesized by known methods (such as phosphotriester, phosphite, or phosphoramidite chemistry, using solid-phase techniques such as described in EP 266,032 published 4 May 1988, or via deoxynucleoside H-phosphonate intermediates as described by Froeshler et al., Nucl. Acids, Res., 14:5399-5407 (1986)). Further methods include the polymerase chain reaction defined below and other autoprimer methods and oligonucleotide syntheses on solid supports. All of these methods are described in Engels et al., Agnew. Chem. Int. Ed. Engl., 28:716-734 (1989). These methods are used if the entire nucleic acid sequence of the gene is known, or the sequence of the nucleic acid complementary to the coding strand is available. Alternatively, if the target amino acid sequence is known, one may infer potential nucleic acid sequences using known and preferred coding residues for each amino acid residue. The oligonucleotides can be purified on polyacrylamide gels or molecular sizing columns or by precipitation.

"Phage display" is a technique by which variant peptides, polypeptides are displayed as fusion proteins to at least a portion of coat protein on the surface of phage, e.g., filamentous phage, particles. A utility of phage display lies in the fact that large libraries of randomized protein variants can be rapidly and efficiently sorted for those sequences that bind to a target antigen with high affinity. Display of peptide and protein libraries on phage has been used for screening millions of polypeptides for ones with specific binding properties. Polyvalent phage display methods have been used for displaying small random peptides and small proteins through fusions to either gene III or gene VIII of filamentous phage. Wells and Lowman, Curr. Opin. Struct.

Biol., 3:355-362 (1992), and references cited therein. In monovalent phage display, a protein or peptide library is fused to a gene III or a portion thereof, and expressed at low levels in the presence of wild type gene III protein so that phage particles display one copy or none of the fusion proteins. Avidity effects are reduced relative to polyvalent phage so that sorting is on the basis of intrinsic ligand affinity, and phagemid vectors are used, which simplify DNA manipulations. Lowman and Wells, *Methods: A companion to Methods in Enzymology*, 3:2050216 (1991).

A "phagemid" is a plasmid vector having a bacterial origin of replication, e.g., ColE1, and a copy of an intergenic region of a bacteriophage. The phagemid may be used on any known bacteriophage, including filamentous bacteriophage and lambdoid bacteriophage. The plasmid will also generally contain a selectable marker for antibiotic resistance. Segments of DNA cloned into these vectors can be propagated as plasmids. When cells harboring these vectors are provided with all genes necessary for the production of phage particles, the mode of replication of the plasmid changes to rolling circle replication to generate copies of one strand of the plasmid DNA and package phage particles. The phagemid may form infectious or non-infectious phage particles. This term includes phagemids which contain a phage coat protein gene or fragment thereof linked to a heterologous polypeptide gene as a gene fusion such that the heterologous polypeptide is displayed on the surface of the phage particle.

The term "phage vector" means a double stranded replicative form of a bacteriophage containing a heterologous gene and capable of replication. The phage vector has a phage origin of replication allowing phage replication and phage particle formation. The phage is preferably a filamentous bacteriophage, such as an M13, f1, fd, Pf3 phage or a derivative thereof, or a lambdoid phage, such as lambda, 21, phi80, phi81, 82, 424, 434, etc., or a derivative thereof.

In this specification, a number of documents including patent applications and manufacturer's manuals is cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

FIGURES

FIG. 1: Binding study of the fluorescein ZnO-binding peptide VRTRDDARTHRK (SEQ ID NO:16). (A) The ZnO-binding peptide (0.1 mg/ml) and the inorganic powders ZnO or $Fe_2O_3$ were mixed in binding buffer (50 mM Tris/0.5% Tween®/15 mM NaCl (pH=7.6)) during 1 h and then washed overnight with the same buffer. Powder was then examined by optical microscopy with fluorescence. (B) Interaction of ZnO-binding peptide with two types of galvanized steel substrates. The Galva Gi206031 is skinpassed, unchromated and has a Z aspect characterized by very few defects whereas the Galva DX510 is unskinpassed, unchromated, Epassived and has an A aspect with some defects. (C) Interaction of ZnO-binding peptide with pure (i) metallic zinc, (ii) zinc oxide (iii) zinc hydroxide (iv) aluminium or (v) aluminium oxide. Oxides have been formed by heating the zinc substrate 1 min at 200° C. and the aluminium substrate 1 min at 800° C. Hydroxides have been formed by attacking the substrate with NaOH 0.1 M for 10 min at room temperature. All substrates were first saturated with 1% BSA before binding.

Figure 2:
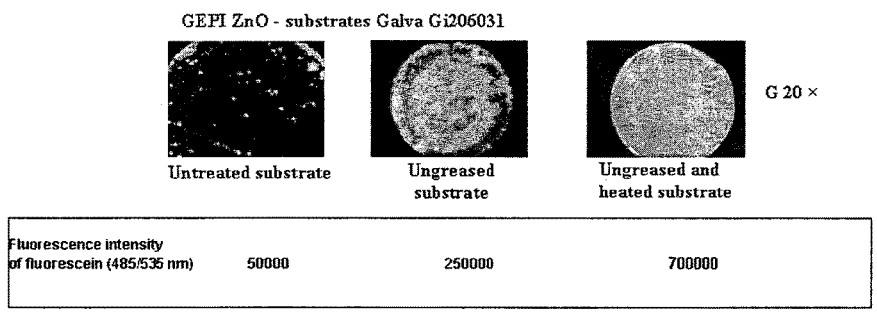

FIG. 2: Effect of alkaline or heating pre-treatment of the substrate galvaGi206031 on its interaction with ZnO-binding peptide. Upper part (left) Untreated substrate i.e washed with a mix ethanol/acetone (Middle) Substrate washed 1 min at 60° C. with 1.5% Novaclean®. (Right) Substrate washed 1 min at 60° C. with 1.5% Novaclean® and heated 2 min at 260° C. Substrates were observed under the optical microscope with fluorescence. The fluorescence intensity of fluorescein was measured at an emission wavelength of 535 nm (λ excitation=485 nm) on 20 horizontal lines per sample. The average intensity was calculated on 10 samples. Lower part: XPS analyses of Galva Gi206031 surface after incubation in binding buffer (50 mM Tris/0.5% Tween®/15 mM NaCl (pH=7.6)) following different washing pre-treatments. (First line) Untreated substrate i.e substrate just washed with a mix 50/50 of ethanol and acetone. (Second Line) Substrate washed 1 min at 60° C. with 1.5% Novaclean®. (Third Line) Substrate washed 1 min at 60° C. with 1.5% Novaclean® and heated 2 min at 260° C. Elemental samples composition are expressed in atomic percentage.

FIG. 3: (Upper part) Study of the cinetic interaction between ZnO-binding peptide (0.1 mg/ml) and the substrate galva206031. Substrates were washed with an alkaline detergent, saturated with 1% BSA and then binding interactions were performed during 1.5, 15 or 60 min. Substrates were then washed overnight with 50 mM Tris/0.5% Tween®/15 mM NaCl (pH=7.6) and observed by microscopy under fluorescence. (Lower part) Desorption study of ZnO-binding peptide on galva206031: effect of extensively washes with acidic or alkaline buffers after peptide-substrate interaction. The ZnO binding peptide (0.1 mg/ml) and the galvanized steel substrate were mixed in binding buffer (50 mM Tris/0.5% Tween®/15 mM NaCl (pH=7.6)) during 1 h and then washed overnight with a buffer at pH 2, 4, 10, or 14 containing Tween 2%. Substrates were then examined by optical microscopy with fluorescence. The last substrate was heated 10 min at 200° C. Fluorescein ZnO peptide in solution under the same conditions is still fluorescent.

FIG. 4: Differential adhesion of ZnO-binding peptide to multiple surfaces. Interaction of ZnO-binding peptide with a partially coated zinc substrate with an Ag 50 nm layer (right part). Ag was deposited on Zn sheet by PVD and masks were placed at some places in order to keep squares of Zn composition. Substrate was submitted to thermal treatment to form the oxide and then binding was performed. (Right part) Observation of the substrate under fluorescence after ZnO-binding peptide recognition.

FIG. 5: Four rounds of panning with the phage display PhD12 kit against stainless steel and $TiO_2$ substrate. The table shows the decrease of phage numbers after each round. About thirty phages were sequenced after the third and fourth round of selection. The consensus peptide sequence for stainless steel and $TiO_2$ are described in the frame. The stainless steel peptide sequence occurred in 70% of clones and the $TiO_2$ sequence in 50% of clones.

FIG. 6: Indirect techniques for measuring the binding of phages containing the consensus sequence to the substrate of interest. (A) Schematic representation of the method used to fluorescently tag the phage. An antibody for the phage coat is linked to biotin. The biotin-streptavidin link is used to attach a streptavidin-conjugated fluorescein to the phage. (B) Fluorescence measurements of the phages containing the stainless steel peptide sequence in interaction with stainless steel substrate (two left circular patches), of the phages containing the Ti peptide sequence in interaction with stainless steel substrate (first right circular patch) and of the phages containing a random peptide sequence in interaction with stainless steel substrate (extreme right circular patch). The intensity of fluorescence is indicated below. (C) Plates resulting from a phage titer showing a clear preference 3: 1 of phages containing the $TiO_2$ peptide for $TiO_2$ substrate compared to the stainless steel substrate.

Figure 7:
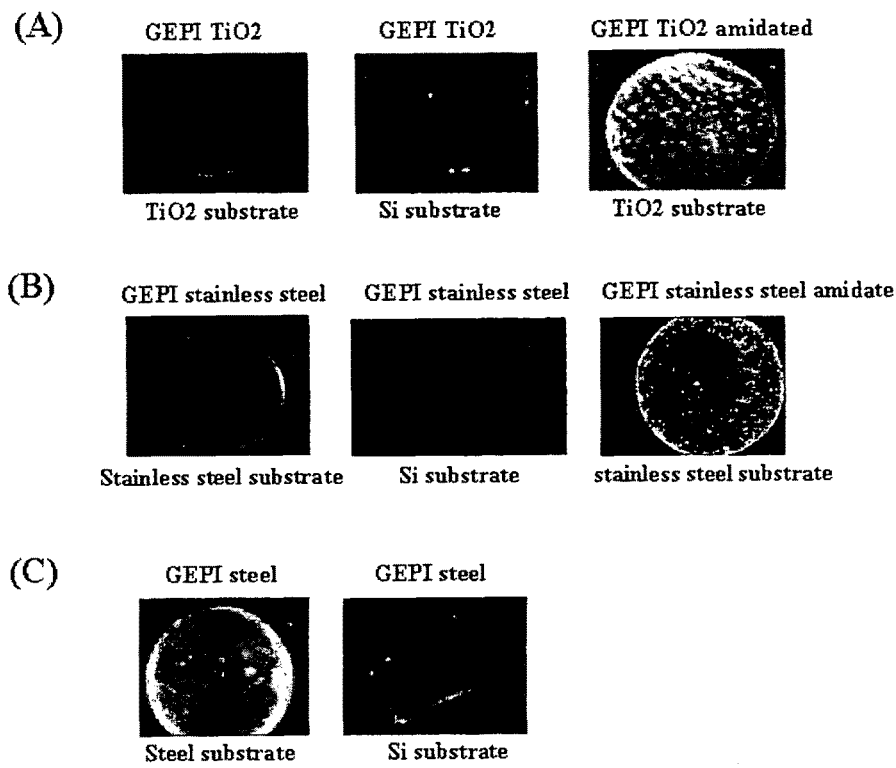

FIG. 7: Interaction of synthetic peptides with a N-terminal fluorescein dye with their respective substrates. (A) Recognition of $TiO_2$-binding peptide with the $TiO_2$ or Si substrate. Recognition of the amidated $TiO_2$-binding peptide for the $TiO_2$ substrate. (B) Recognition of stainless steel-binding peptide for the stainless steel or Si substrates. Recognition of the amidated stainless steel-binding peptide for the stainless steel substrate. (C) Recognition of stainless steel-binding peptide for the stainless steel or Si (negative control) substrates.

Figure 8:
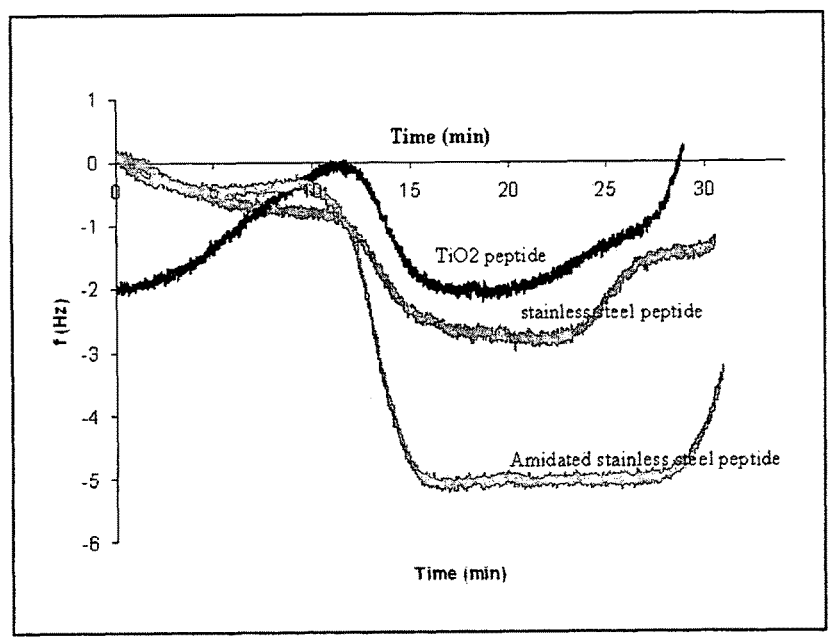

FIG. 8: QCM measurements of the adsorption of synthetic $TiO_2$-binding peptide, stainless steel-binding peptide and amidated stainless steel-binding peptide onto stainless steel substrates. $TiO_2$-binding peptide was used as negative control. The shift in the resonant frequency is plotted as a function of time. QCM sensors were first stabilized in the binding buffer 50 mM Tris/0.5% Tween®/15 mM NaCl (pH=7.6). Peptides were loaded at 5 min time and buffer was injected for rinsing once the adsorption curve stabilized.

Figure 9:
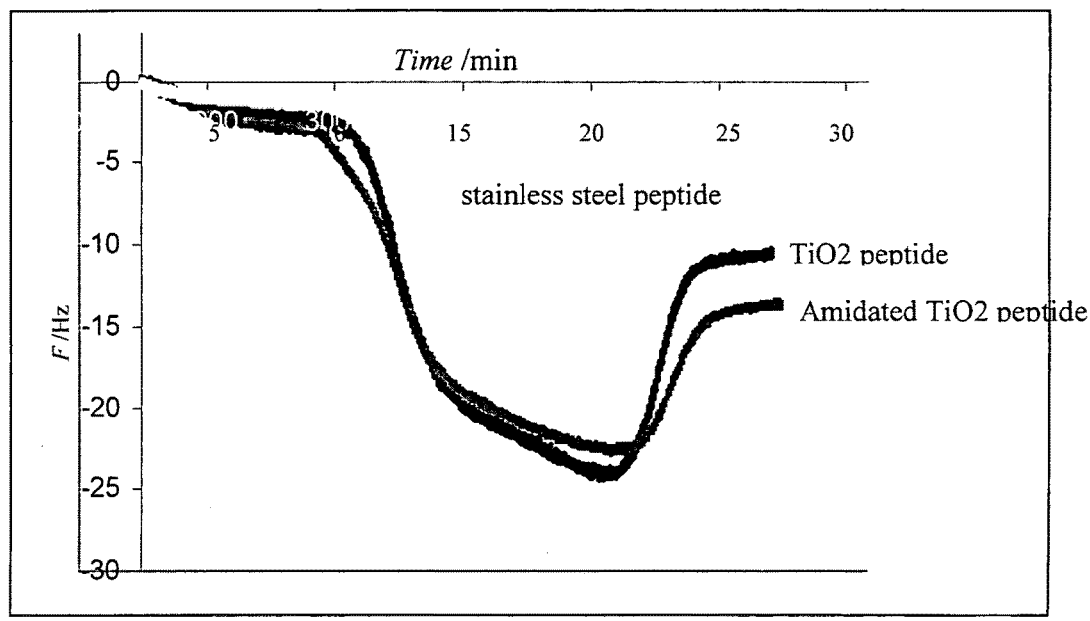

FIG. 9: QCM measurements of the adsorption of synthetic stainless steel-binding peptide, $TiO_2$-binding peptide and amidated $TiO_2$-binding peptide onto $TiO_2$ substrates. Stainless steel-binding peptide was used as negative control. The shift in the resonant frequency is plotted as a function of time. QCM sensors were first stabilized in the binding buffer 50 mM Tris/0.5% Tween®/15 mM NaCl (pH=7.6). Peptides were loaded at 5 min time and buffer was injected for rinsing once the adsorption curve stabilized.

Figure 10:
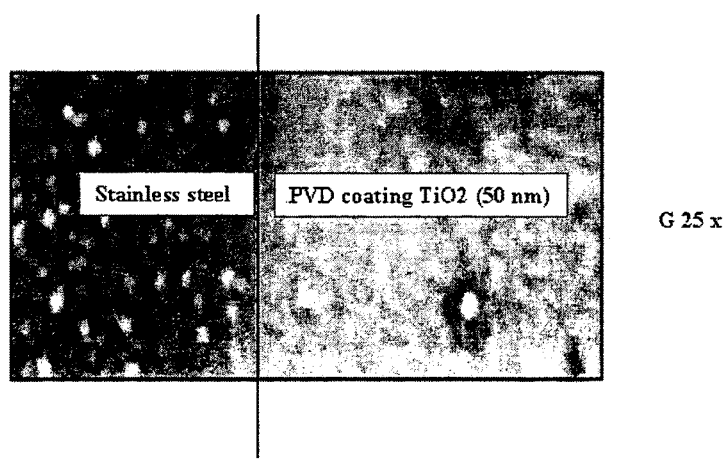

FIG. 10: Differential adhesion of $TiO_2$/stainless steel-binding peptide to multiple surfaces. $TiO_2$-fluorescein synthetic peptide was incubated with a substrate composed of a left part made of stainless steel and a right part made of $TiO_2$.

FIG. 11: Available strategies in order to operate the sorting of a nanopowder mixture. In one approach (FIG. 11A) the GEPI targeted towards particles X is added to the aqueous suspension of a blend of particles X and Y to be sorted. GEPI will anchor specifically onto particles X. In a first example (FIG. A1), the aqueous dispersion of particles Y and [particles X-GEPI] can be further processed on a support displaying a great affinity for the GEPI or even more generally for amino acids based molecules: particles Y will stay in suspension and particle X will be retrieved after elution from the affinity support. In a second example, the inorganic binding peptide (GEPI) comprises a tag; such as for example a histidine tag or any other chemical or biological moiety allowing for further affinity binding to an adequate complementary support; examples are biotin-streptavidin like systems or histidine-metal ions like systems. In still another example, GEPI can be grafted with a superhydrophobic/philic chemical or biological adduct and the sorting could be processed based on this newly induced physico-chemical specific characteristic of the complex [particle X-GEPI-adduct]. In another approach (FIG. 11B), the GEPI targeted towards particles X is linked/grafted to a support and the blend of nanoparticles adequately dispersed in an aqueous suspension is processed onto the functionalized support. In one example (FIG. B2) GEPI could be grafted onto a macroporous material framework being organic, inorganic or biological in nature; the suspension of nanoparticles to be sorted is contacted/sieved with the functionalised framework, particles X instantly link/stick to GEPI-X and particles Y flow through. In an alternate example (FIG. B1) GEPI can be immobilized onto a matrix like beads for chromatography or on a resin or on a membrane of any type of chemical composition and any physical form; consequently the suspension of nanoparticles to be sorted is filtered/sieved onto the functionalised matrix, resin, membrane (tangential filtration for example), particles X instantly link/stick to GEPI-X and particles Y flow through. The functionalized framework or matrix can also be ceramic tubes or any other.

Having generally described the invention, the same will be more readily understood by reference to the following examples, which are provided by way of illustration and are not intended as limiting.

Example 1

Materials and Methods

Material

ZnO (99.99%), $Fe_2O_3$ (99.98%) and $Cu_2O$ (99.9%) powders were purchased from Sigma-Aldrich. Galvanized steel substrates were supplied by the ArcelorMittal steel company. Galvanized substrates have their surfaces recovered by a thin ZnO layer to prevent corrosion. The galvanized steel reference Gi206031 is skinpassed, unchromated and has a Z aspect (few defects on the surface, good quality). The galvanized steel reference DX510 is unskinpassed Le heterogeneous roughness, chromated, E-passived with a thin layer of phosphate and has an A aspect (more defects). Galvanized steel substrates were characterized by Auger and time-offlight (TOF)-SIMS spectroscopy (data not shown). Pure (99.9%) metal sheet of Zn, Si, Ag and Al were purchased by Goodfellow (Germany). Fluorescein sodium salt was bought from Fluka (Germany). The ZnO-binding peptide VRTRDDARTHRK (SEQ ID NO:16) with a fluorescein dye in N-terminal comes from Eurogentec (Liege, Belgium).

The phage display kits PhD12 and PhDC7C were purchased from New England Biolabs. Stainless steel and $TiO_2$ substrates were offered by ArcelorMittal. Stainless steel is an alloy CrFe—Ni. The $TiO_2$ substrate is a 50 nm amorphous physical vapour deposition (PVD) coating on a stainless steel substrate. Two types of substrate configuration were used. The first three rounds of selection were done on a 5 mm diameter disks of inorganic substrate whereas the fourth round was performed in a 5 mm depth molded in a stainless steel or $TiO_2$ sheet.

Media

Tween®-20 (Sigma-Aldrich), isopropyl-β-D-thiogalactosidase (IPTG) (Eurogentec, Liege, Belgium), 5-bromo-4-chloro-3-indoyl-β-D-galactosidase (X-Gal) (Eurogentec, Liege, Belgium), tetracycline (Fluka), PEG-8000 (Sigma-Aldrich) anti-fd antibodies were purchased by Sigma-Aldrich. Streptavidin-conjugated fluorescein was purchased from Molecular Probes.

Peptide Preparation

Peptides were solubilized in 50 mM TrisIO.5% Tween®/ 15 mM NaCl (pH=7.6) binding buffer at a concentration of 0.1 mg/ml.

Substrates Preparation

Powders were washed with binding buffer before interaction. Galvanized steel substrates were first washed 10 min with a mix of ethanol/acetone and then with Novaclean® 271F 1.5% during 1 min at 60° C. Novaclean® is a commercial alkaline detergent (Arnaud group, France). Pure Zn and Al sheets were washed 10 min with a mix of ethanol/ acetone. The metal oxide was formed by heating the zinc substrate 1 min at 200° C. and the aluminium substrate 1 min at 800° C. Hydroxides were formed by attacking substrates with NaOH 0.1 M 10 min at RT. Stainless steel and $TiO_2$ substrates were washed with a mix of acetone/ethanol. All substrates were then washed with water and incubated in binding buffer before peptide interaction.

Binding Studies

All washed substrates or powders were saturated for 2 h with 1% BSA before binding. The ZnO-binding peptide (0.1 mg/ml) and the inorganic powders/substrates were mixed in 50 mM Tris/0.5% Tween®/15 mM NaCl (pH=7.6) binding buffer for 1 h and then washed overnight with a 50 mM Tris/0.5% Tween®/15 mM NaCl (pH=7.6) buffer. Stainless steel and $TiO_2$ substrates were contacted with stainless steel/$TiO_2$-binding peptide (0.1 mg/ml) and incubated in binding buffer (50 mM Tris/0.5% Tween®/15 mM NaCl (pH=7.6)) for 1 h and then washed overnight with a 50 mM Tris/0.5% Tween®/15 mM NaCl (pH=7.6).

Microscope Analyses

After binding, powder/substrates were examined by optical microscopy with fluorescence. Confocal imaging was performed using a Leica TCS SP2 inverted confocal laser microscope (Leica Microsystems, Germany). Digitized images were acquired using a 63× (NA 1.2). Fluorescein was visualized by using an excitation wavelength of 488 nm and the emission light was recorded at 535 nm. The acquisition was set up to avoid any cross-talk of the three fluorescence emissions. Series of optical sections were carried out to analyze the spatial distribution of fluorescence, they were recorded with a Z-step ranging between 1 and 2 µm. Image processing, including background subtraction, was performed with Analyses software (version 2.5).

XPS Analyses

XPS measurements were performed on an electron spectrometer for the multi-technique surface analysis system. This system is equipped with a double stage cylindrical mirror electron energy analyzer. The photon source is a Cameca SCX 700 dual anode X-ray source. A non-monochromatized Al Kα X-ray source (hv=1486.6 eV) is used as the excitation source in all cases. Using the Au $4f_{7/2}$ and Cu $2p_{3/2}$ photoelectron lines, a spectrometer energy calibration was performed. Surface electrostatic charges were detected for some samples, which resulted in variable retarding effects, thus all the energy scales corresponding to the XPS spectra reported were normalized from the energy position of the C 1 s photoelectron line of atmospheric carbon $(CH_2)_n$: 285 eV. The photoemission measurements were carried out on a series of samples before and after partially removing the surface carbon contamination by ion sputtering. The sputtering was performed for 10 min in the ultra high vacuum (UHV) analysis chamber with a 0.6 keV $Ar^+$ ion beam (30 mA $cm^{-2}$). The elemental sample compositions were evaluated by XPS using the integrated areas of the core-level peaks C 1s, N 1s, O 1s, Al 2p, Ca 2p3, Cu 2p3, Zn 2p3. The molar fractional content $X_i$ of one element i (with i=0, C . . . ) in an analyzed substrate was calculated with the relation: $X_i = A_i/S_i / \Sigma A_i/S_i$ with $A_i$ the area of the peak related to the atom i, and $S_i$ the sensitivity factor of the atom i.

Selection of Inorganic Binding Peptides by Phage Display

Experiments were performed according to the panning procedure described in the protocol of the kits PhD12 or PhDC7C Biolabs kit. Four rounds of biopanning were conducted for either stainless steel or $TiO_2$ substrates in order to extract consensus peptides. The eluted phages from the fourth round were tittered on agar plates and about 30 individual phage clones were sampled to recover peptide sequences.

DNA Sequencing

S Sequencing of the M13 phages after 4 rounds of selection was performed with the 96 gIII reverse sequencing primer (5'-CCC TCA TAG TTA GCG TAA CG-3' (SEQ ID NO:30)).

Measurement of Phage-Substrate Affinity with (i) Fluorescent Antibodies

Substrates were exposed to 20 µl of phage ($10^6$ phage/µl determined by titration). After 30 minutes, samples received a Tris-buffered saline containing 1% BSA and 0.5% Tween®-20 (TBST-BSA) intermediate wash. Next samples were exposed to 20 µl of biotinylated anti-fd (1/50 dilution of the stock solution) for 30 minutes. A second intermediate wash was performed and samples were finally exposed during 30 minutes to 20 µl of streptavidin-conjugated fluorescein (1/100 dilution of the stock solution). Samples then received a final wash with 4×TBST-BSA, 4×TBST, 4×TBS, 4× $H_2O$.

(ii) Titration Measurements

Substrates were exposed to 20 µl of phage ($10^6$ phage/µl determined by titration). After 30 minutes, samples received a TBS/1% BSA/0.5% Tween®-20 intermediate wash. Phage were then eluted at pH 2 and titered as described in the phage display kit. The results of the titration were plates with blue viral plaques. The number of plaques corresponded to the number of phages which bound to the substrate. The phage population was diluted before plating so that the number of plaques on a given plate could be counted by hand.

Measurement of Peptide Affinity for Substrate with (i) A Fluorescein Dye

The three consensus sequences were ordered by Eurogentec (Liege, Belgium) with the fluorescein dye in N-terminal. Synthetic peptides were solubilized in 50 mM Tris/0.5% Tween®/15 mM NaCl (pH=7.6) binding buffer and put in contact with respective substrates as described in the binding section. Substrates were characterized by microscopic analyses.

(ii) QCM-D Measurements

A QCM consists of a thin quartz disc sandwiched between a pair of electrodes. The resonant frequency of the crystal, when excited by an AC voltage, depends on the total oscillating mass, including coupled water. QCM thus provides a measure of the "wet mass". A "soft" (viscoelastic) adsorbed layer will dampen the crystal's oscillation. The dissipation may be measured at multiple frequencies and by applying a viscoelastic model, the mass, thickness, elastic shear modulus, and shear viscosity of the adhering film can be determined. Our QCM-D instrument (D300, Q-Sense, Sweden) is composed of a parallel plate flow cell whose bottom surface is a QSX 303 Sensor Chip (Q-Sense). Stainless steel and Ti quarts crystal were used. The 5-MHz AT cut quartz crystal was coated on one side with Ti (Q-sense AB, catalog No QSX3I0) for Ti-peptide measurements. Chemical composition of electrodes was confirmed by XPS analyses (XPS spectrum not shown). The QCM measurements were conducted at a flowrate of 25 µl/min in a stagnant liquid cell where the solution contacts the stainless steel or Ti side of the quartz crystal sensor. For each measurements, 50 mM Tris/0.5% Tween®/15 mM NaCl (pH=7.6) binding buffer was first loaded into the liquid cell. Following the achievement of stable baselines for f and D, synthetic peptide solution diluted in the same buffer was added into the liquid cell to replace the binding buffer. The concentration of peptide samples used in the QCM-D measurements was adjusted to 0.1 mg/ml. The fl 1 values were presented for analyses.

Example 2

2.1 Binding Study of ZnO-Binding Peptide with Galvanized Steel Substrates

Binding study of a fluorescein solution (0.1 mg/ml) with ZnO powder and galvanized steel substrates show that the dye alone has no affinity for our substrates. Fluorescein was then covalently linked to the N-terminal end of the ZnO peptide VRTRDDARTHRK (SEQ ID NO:16) to visualize all peptide-substrate interaction. Binding experiments were first performed on powders. Peptide (0.1 mg/ml) was incubated with ZnO powder in 50 mM Tris/0.5% Tween®/15 mM NaCl (pH=7.6) binding buffer during 1 h, powders were washed overnight with the same buffer and examined by optical microscopy with fluorescence. As shown in FIG. 1A, ZnO-peptide specifically interacts with ZnO powder. A low residual interaction is observed with $Fe_2O_3$ powder.

The interaction between ZnO-binding peptide and 2 types of galvanized steel flat surfaces was then studied. Galvanized substrates are known to be covered with a thin layer of ZnO in order to prevent corrosion. The two galvanized substrates were (i) Galva Gi206031 which is skinpassed, unchromated and with a Z aspect characterized by very few defect and (ii) a Galva DX510 which is unskinpassed, unchromated, E-passived and with a A aspect characterized by some defects. Interestingly, the inorganic-binding peptide strongly binds to both galvanized substrates (FIG. 1B) but with different recognition profiles in function of the surface quality. No interaction was observed with the negative control Si surface.

In order to highlight the specificity of ZnO-binding peptide for the ZnO component and to get rid of inhomogeneity and instability characteristics of galvanized surfaces, experiments were performed on pure zinc sheets treated in order to have (i) pure metal (ii) pure zinc oxide or (iii) pure zinc hydroxide. Aluminium and aluminium oxide flat sheets were used as negative controls. FIG. 1C shows that ZnO-peptide recognizes the zinc oxide form with high specificity.

Surface pre-treatment is also an important parameter to characterize in the field of galvanized substrates. Galvanized steel substrates were submitted to several washing conditions and then incubated with fluorescent ZnO-binding peptides. It appears that the affinity of ZnO binding peptide for galvanized steel substrate is increased after alkaline and heating pretreatment of the substrate. The intensity of fluorescence of peptide bound to substrate submitted to alkaline wash is 5-fold higher than on original substrate. Moreover, there is a 3 fold fluorescence increase if the substrate has been heated after alkaline wash (FIG. 2).

In summary, labelled ZnO binding peptides appear as good markers for chemical composition defects on galvanized steel substrates and for pre-treatment efficiency verification.

2.2 Galvanized Steel Surface Characterization

In order to figure out why ZnO-binding peptide recognizes degreased and/or heated substrates with higher affinity, XPS analyses were performed. Table 3 below (as well as Figure) gives the atomic percentage of each element at the surface of galvanized steel submitted to (i) an acetone/ethanol wash, (ii) an alkaline detergent wash and to (iii) an alkaline wash plus a heating at 260° C. As you can see, the atomic percentage of aluminium on substrate washed with a mix of acetone and ethanol is high compared to the zinc percentage. This result explains why the fluorescence intensity is low. After alkaline wash, the atomic percentage of aluminium dramatically decreases to the great benefit of the zinc percentage. After alkaline wash and heating, the effect is even stronger, the amount of aluminium is nearly zero and the percentage of zinc reaches a maximum. In summary, the atomic percentage of zinc and aluminium on galvanized steel surfaces is in good correlation with the fluorescence intensities of ZnO-peptides.

TABLE 3

Atomic percentage of each element at the surface of galvanized steel submitted to (i) an acetone/ethanol wash (untreated substrate), (ii) an alkaline detergent wash (ungreased substrate) and to (iii) an alkaline wash plus a heating at 260° C. (ungreased and heated substrate).

| XPS analyses of Galva Gi206031 substrate in binding buffer | C1s (% at) | N1s (% at) | O1s (% at) | Al2p (% at) | Ca2p3 (% at) | Cu2p3 (% at) | Zn2p3 (% at) |
| --- | --- | --- | --- | --- | --- | --- | --- |
| Untreated substrate | 61.81 | 0.78 | 24.07 | 9.54 | 0.17 | 0 | 2.55 |
| Ungreased substrate | 46.08 | 1.44 | 33.39 | 0.7 | 0.26 | 0.45 | 15.92 |
| Ungreased and heated substrate | 50.51 | 0.51 | 28 | 0.23 | 0 | 0 | 19.55 |

To check if the different intensity profiles are not due to differences in substrate wettability, contact angles between water and galvanized steel surfaces submitted to different washing conditions were measured. A value of 79.1°±2.6 was found for substrates washed with ethanol, a value of 7.5°±0.2 for substrates washed with alkaline detergent and a value of 73.6°±2.8 for substrates ungreased and heated. By consequence, differences in intensity are not due to differences in substrate wettability because high profile intensity may be observed with low or high contact angles.

2.3 Kinetic, Strength and Durability of ZnO Peptide-Galvanized Steel Surface Interaction The kinetic, strength and durability of ZnO-binding peptide interaction with galvanized steel surface reference Gi206031 was considered. In that aim, ZnO-peptides were mixed during 1, 5, 15, or 60 min with substrate and then washed overnight. As shown in FIG. 3, the recognition is really fast and has reached its maximum level after 1 min of binding contact.

The binding force of ZnO-binding peptide for the galvanized steel substrate was then investigated. Substrates dipped into ZnO-binding peptides were then extensively washed with acidic or alkaline buffer and the residual fluorescence was measured. The thermal resistance of the binding was also investigated. FIG. 3 shows that the peptide-substrate interaction is strong, peptides persist on the substrate after washes with buffer at pH 10 and 4. Thermal treatment only partially disrupts the interaction. Peptides are only removed from galvanized substrate after extensively washes with a pH 2 or 14 buffer. Peptide itself is still fluorescent under the same pH and thermal conditions. The durability of the peptide coating on steel was then investigated by measuring the intensity of fluorescein-peptides bound on steel surfaces after 2 weeks. Sample fluorescence decreases by a 2 fold factor after 2 weeks at room temperature, but fluorescein alone in the same conditions undergoes the same decrease due to photobleaching (Boxer, 1979).

2.4 Differential Adhesion of ZnO-Binding Peptides to Inorganic Surfaces

In order to highlight the differential adhesion of ZnO-binding peptides to multiple surfaces, a patterned substrate was constructed consisting in a 50 nm layer of silver deposited by PVD on a pure zinc sheet with masks at some places in order to keep zinc squares. Substrate was submitted to thermal treatment to form an oxide layer and binding was performed. As shown in FIG. 4, ZnO-binding peptide recognizes the ZnO area with a ten times higher affinity than the silver oxide area. The edges of the square are irregular which is highlighted by fluorescent peptide binding.

At this stage, fluorescent ZnO-binding peptide appears as good defect detector tool on galvanized steel surfaces. In order to validate this concept on other type of inorganic surfaces, peptides were isolated against two others inorganic surfaces (stainless steel and amorphous $TiO_2$) and use to detect coating defects.

Example 3

Selection of $TiO_2$ and Stainless Steel Binding Peptides and their Use as Quality Control Detectors 3.1 Selection of Stainless Steel and $TiO_2$ Binding Peptides by Phage Display A library of viruses expressing random peptide sequences was exposed to the inorganic substrate of interest: stainless steel and amorphous $TiO_2$ surfaces. Two different libraries from Biolabs were tested: PhD12 and PhDC7C. Both libraries are based on the M13 bacteriophage expressing a modification on the minor coat protein as pIII. M13 is a filamentous phage with a capsid composed of roughly 2700 copies of the major coat protein (pVIII). The modified pIII protein is expressed at one end of the viral assembly and has five copies. At the end of each of these copies is the random peptide fusion that used to identify through selection. The phage display library PhD12 utilize a twelve amino acid unconstrained library. The phage display library PhDC7C containing a seven amino acid constrained library was also tested. Constrained refers to the fact that the random peptide sequence is flanked by cysteines. The cysteines form a disulfide linkage that forces the peptide fusion into a ring-like structure. This limits the space of conformational freedom available to the peptide thus ensuring a more specific fit to the substrate. Experiments were then repeated with this PhDC7C kit in order to select peptides with higher affinity for the substrate. The diversity of those libraries is respectively $2.7 \times 10^9$ for the PhD 12 kit and $1.2 \times 10^9$ for the PhDC7C.

3.2 Selection on a New Shaped Surface.

The first selection steps were performed on 5 mm diameter stainless steel or TiO2 disks and sampled the whole surface (upper and lower faces plus edges) of the disks with no discrimination between the upper/lower faces and the edges. The edges are made of stainless steel for both samples, they are not coated by $TiO_2$. After three rounds of selection on circular patch substrate, a last round of selection was performed in the 5 mm-depth well of a stainless steel or $TiO_2$ sheet. This complementary surface displays no edges and is totally coated. By keeping the phages that do not bind to this surface, we isolated peptides that recognize stainless steel. By opposition, by keeping the phages that recognize this surface, peptides recognizing $TiO_2$ are isolated.

3.3 Sequencing after Four Rounds of Panning.

In the first experiment with the PhD12 kit, about thirty phage were sequenced after three or four rounds of selection. The reduction in library diversity and subsequent enrichment for the consensus sequence is reflected in Table 4 below. This resulted in a consensus peptide sequence for stainless steel and $TiO_2$. The stainless steel binding peptide sequence MTWDPSLASPRS (SEQ ID NO:31) occurred in 70% of clones and the $TiO_2$ binding peptide sequence LNAAVPFTMAGS (SEQ ID NO:32) in 50% of clones (FIG. 5). Panning experiments were also performed with the PhDC7C library. Three rounds of selection were performed in the 5 mm depth well of the substrate sheet. The diversity of the library decreased rapidly. The number of selected phages after three rounds of selection is zero. Sequencing was then done after two rounds of panning. No consensus sequence was highlighted. This result can be explained by the fact that the disulfide loop imposed structural constraint to randomized peptides and may "freeze out" a conformation required for target binding.

TABLE 4

Reduction in library diversity and subsequent enrichment for the consensus sequence after up to four rounds of selection.

| | Phage number | | | | |
|---|---|---|---|---|---|
| | Start | Round 1 | Round 2 | Round 3 | Round 4 |
| Stainless steel substrate | $2.7 \cdot 10^9$ | $10^7$ | $2 \cdot 10^5$ | $5.10^3$ | 100 |
| TiO2 substrate | $2.7 \cdot 10^9$ | $10^7$ | $2 \cdot 10^5$ | 100 | <100 |

3.4 Measurement of the Phage Affinity for the Corresponding Substrate

Indirect techniques were employed to verify the binding of the phages containing the consensus sequence to the substrate of interest. The first technique involves fluorescent tagging of phages that are bound to the substrates and then measuring the substrate fluorescence as an indirect measure of the attached phage concentration. First, efforts were focused on the consensus peptide sequence recognizing stainless steel. Phages containing either peptides recognizing $TiO_2$ or random peptide were used to control non-selective background binding. All three phages were fluorescently tagged using an antibody for the phage (biotinylated anti-fd) which is linked to a fluorescent dye (streptavidin-conjugated fluorescein via the biotinstreptavidin linkage) (FIG. 6A). The specificity of the stainless steel peptide was investigated. The fluorescence measurements showed a roughly 3:1 preference of the stainless steel peptide for the stainless steel substrate compared to the $TiO_2$ peptide. The fluorescence signal from M13KE with random peptide sequence is in the same range as the phage with $TiO_2$ peptide (FIG. 6B). Second, the same experiment was performed on $TiO_2$ substrates and same results were obtained (data not shown).

The second technique is titration. Titration is a quantitative technique for measuring the number of phages that bind to a substrate. No antibody or fluorescent dye was needed for titration. We took advantages from the lacZ gene present in the phage genome for counting the phages recognizing the substrate on IPTG/X-gal plates. Here we focused on phages containing the $TiO_2$ peptide in order to characterize their affinity for the $TiO_2$ substrate. The resulting plates indicated a 3:1 preference for the $TiO_2$ substrate compared to the stainless steel substrate (FIG. 6C). These last results are in agreement with intensity values obtained previously with M13 fluorescent antibodies.

3.5 Measurement of the Synthetic Peptide Affinity for the Corresponding Substrate.

In order to characterize the affinity of the chemically synthesized peptide (EGT, Liege, Belgium) for its substrate, a fluorescein dye was added at the N-terminal end of the peptide. The recognition of GEPI $TiO_2$ for the $TiO_2$ substrate is low (FIG. 7A) as well as the recognition of GEPI stainless steel for the stainless steel substrate (FIG. 7B). The low binding efficacy of the synthetic peptide for the corresponding substrate could be explained by the fact that the C-terminus of the peptide was neutral and fused in the phage whereas it is free and negatively charged in the synthetic peptide which may completely abolish binding. To confirm this hypothesis, the C-terminal carboxylate of synthetic peptide was amidated to block the negative charge. FIGS. 7A and 7B show that amidation dramatically increases the interaction of the synthetic peptides for their respective substrates.

3.6 Quantitative Analyses of Stainless Steel/$TiO_2$ Binding Peptide Affinity for the Corresponding Substrate by QCM-D The adsorption behaviour of stainless steel/$TiO_2$ binding peptide onto stainless steel/$TiO_2$ electrode was studied by QCM-D and showed that synthetic peptides do adsorb on the electrode surface with different affinities: frequency shift after adsorption of $TiO_2$ peptides on $TiO_2$ substrates is equal to 25 Hz whereas frequency shift after adsorption of stainless steel peptides on stainless steel substrates is equal to 5 Hz (FIGS. 8 and 9) which means that $TiO_2$ binding peptides have a higher affinity for their substrates than stainless steel peptides for stainless steel substrate. Moreover, $TiO_2$ binding peptide has a good remanence on its support during washing whereas stainless peptides do not. Moreover, it has to be noticed than amidation of stainless steel or $TiO_2$ binding peptides lead to an increased affinity for their substrates or an increased resistance to washing.

3.7 Differential Adhesion of $TiO_2$/Stainless Steel Binding Peptides to Multiple Surfaces.

Patterned substrate consisting of a 50 nm TiO2 PVD coating on the right part of a stainless steel sheet substrate, the left part remaining stainless steel showed that $TiO_2$ peptide has a 3-fold higher recognition profile for the $TiO_2$ substrate area compared to the stainless steel area (FIG. 10). As shown in FIG. 8, $TiO_2$ binding peptides only have a low affinity for stainless steel substrates. The frequency shift after adsorption is about 2 Hz which is too small to be detected by fluorescence. By consequence, the small fluorescent zones observed on stainless steel area of FIG. 10 after $TiO_2$ binding peptide adsorption are not due to a lack of specificity of $TiO_2$ binding peptides, but probably due to a small contamination during coating. At the same time, stainless steel binding peptides were incubated on the same patterned substrate and a 3-fold higher recognition profile for the stainless area compared to the $TiO_2$ area was also observed (data not shown).

4. Nanopowder Sorting 4.1 Sorting of Inorganic Insoluble Powders of Different Chemical Composition in Accordance with the Invention In accordance with the invention, inorganic binding peptides were used in an effort to isolate the chemical form of interest in a mixture of inorganic powders. The inorganic powder mixture has to be insoluble and well dispersed in aqueous media to ensure good recognition. In this example, the ZnO-binding peptide (VRTRDDARTHRK) identified by Kjaergaard in 2000 and synthesized by Genescript (Piscataway, USA) was used to isolate the ZnO chemical form from a mixture of ZnO and $Cu_2O$ insoluble powders. In that aim, an amino group of the ZnO-binding peptide (120 µg) was first bound to the epoxy group of the Dynabeads® M-270 magnetic beads (6 mg, $4 \cdot 10^8$ beads) (Invitrogen) according to manufacture procedure. Peptide binding to magnetic beads was visualized by optical microscopy under fluorescence thanks to the FITC dye attached to the N-terminal end of the GEPI ZnO. An excess of peptide functionalized beads was then incubated during 1 h with a well dispersed and stable ZnO and $Cu_2O$ powder mixture (see table 5 for the respective amounts). Optimal dispersion parameters (Tween®-20 1.5%, sonication at 30% during 5 minutes) of both ZnO and $Cu_2O$ insoluble powders were determined by granulometry (Malverne Master sizer 2000). Once the functionalized beads are in contact with the powder mixture, the ZnO insoluble powder should bind to functionalized magnetic beads whereas $Cu_2O$ powder should remain in the flow through. After 1h incubation of the functionalized beads with the powder mixture, the beads were washed with PBS buffer and beads and buffer were separated by magnetization. This washing/separation step repeated 10 times. The chemical composition of the pull of washed fractions was analyzed by atomic adsorption. Powders bound to the functionalized magnetic beads were eluted by a citrate buffer (pH 3, 0.1 M) and separated by magentisation. Two elution steps were performed. The pull of eluted fractions was analysed by atomic adsorption. Chemical composition of initial fractions as well as washed (10 times with PBS) and eluted (pH 3, 0.1 M citrate solution) fractions are given in table 5. The experiment was repeated several times with a fixed amount of beads and various amounts of ZnO and $Cu_2O$. Two examples of results are given in table 5.

TABLE 5

ZnO insoluble powder separation from a ZnO:$Cu_2O$ mixture via ZnO inorganic binding peptides bound to magnetic beads. Atomic adsorption analyses of Cu and Zn composition in the initial, washed or eluted fractions.

| | Zn (mg/l) | Cu (mg/l) | % Zn | % Cu |
|---|---|---|---|---|
| Experiment 1 | | | | |
| Initial amount | 900 | 4415 | 100 | 100 |
| Washed fractions | 421 | 5319 | 46.7 | 120.4 |
| Eluted fractions | 543 | 154.1 | 60.2 | 3.4 |
| Experiment 2 | | | | |
| Initial amount | 3450 | 5400 | 100 | 100 |
| Washed fractions | 1336 | 5572 | 40.1 | 103 |
| Eluted fractions | 1825 | 49.5 | 52.8 | 0.9 |

These results prove that inorganic binding peptides can be used as tools to separate an insoluble inorganic powder from an insoluble powders mixture of various chemical compositions. In this example, the sorting is performed thanks to the ZnO binding peptide bound to magnetic beads. The initial ZnO:$Cu_2O$ mixture is enriched in the ZnO form by a 18 (experiment 1) to a 58 (experiment 2) times factor in a one step procedure depending on the initial amount of ZnO and $Cu_2O$.

4.2 Preliminary Trials with ZnO and Cu₂O Powders

Preliminary trials were run with ZnO and Cu₂O powders. The aim of the experiment was to separate the ZnO powder from an insoluble mixture of ZnO and Cu₂O. ZnO binding peptide previously described in this application was prepared in adequate quantities and anchored via its amino group onto the epoxy group of magnetic beads according to manufacture procedure (Dynabeads, Invitrogen). The inorganic peptide mediated the interaction between the magnetic beads and the target powder. The peptide functionalized magnetic beads are put in contact with the ZnO and Cu₂O mixture and used to isolate the ZnO powder from the ZnO—Cu₂O mixture by simple magnetisation. The complete recognition and separation process is described in details above. Moreover, this technology can be expanded to the sorting of other inorganic insoluble particles including but not limited to Fe(IO3)3, barium titanate and carbon nanotubes. GEPI recognizing the powder of interest has first to be isolated by phage display. Once identified, the specificity of the inorganic peptide has to be highlighted.

4.3 Preliminary Trials with Al₂O₃ Nanopowders

Preliminary trials are run with Al₂O₃ nanopowders of rhomboedral or cubic crystalline form (20-30 nm size). Inorganic binding peptides recognizing specifically each of the 2 crystallographic forms are selected using phage display techniques. Two different libraries from Biolabs are tested: PhD12 and PhDC7C. Both libraries are based on the M13 bacteriophage expressing a modification on the minor coat protein pIII. M13 is a filamentous phage with a capsid composed of roughly 2700 copies of the major coat protein (pVIII). Five copies of the modified pIII protein are expressed at one end of the viral assembly and at the end of each of these copies is the random peptide fusion that we try to identify through selection.

Once the 2 peptides recognizing specifically each of the 2 crystallographic forms are identified and prepared in adequate quantities, they are anchored onto the surface of particles with high magnetophoretic mobilities. The inorganic-binding peptide mediates the interaction between the magnetic particle and the target nanoparticle. Inorganic-binding peptides are anchored onto amine or carboxylic acid modified silica encapsulated iron oxide nanoparticles. Magnetic particle also carry a luminescent marker. Another approach is to graft the inorganic binding peptide onto agarose beads and operate target nanopowder sorting out of aqueous slurry following either a batch or column process.

The technology can be expanded to the sorting of other nanoparticles including, but not limited to, Fe(IO₃)₃, Barium Titanate (ferro-electric oxides), and carbon nanotubes.

REFERENCES

Brown, S. (1997) Nature Biotechnology (15), 269-272
Chen, H., Su, X., Neoh, K. G., Choe, W. S. (2006) Anal. Chem. 78(14): 4872-4879
Gaskin, D. J. H., Starck, K., Vulfson, E. N. (2000) Biotechnology Letters 22: 1211-1216,
Jószai V, Nagy Z, Osz K, Sanna D, Di Natale G, La Mendola D, Pappalardo G, Rizzarelli E, Sóvágó I. J Inorg Biochem. 2006 August; 100(8):1399-409. Transition metal complexes of terminally protected peptides containing histidyl residues.
Lee, W. S., Mao, C., Flynn, C. E., Belcher, A. M. (2002) Science (296), 892-895.
Mao, C., Flynn, C. E., Hayhurst, A., Sweeney, R., Qi, J., Georgiou, G., Iverson, B., Belcher, A. M. (2003) PNAS 100(12): 6946-6951
Mao, C., Solis, D. J., Reiss, B. D., Kottmann, T., Sweeney, R. Y., Hayhurst, A., Georgiou, G., Iverson, B., Belcher, A. M. (2004). Science (303), 213-217.
Naik, R. R., Lawrence, L. B., Clarson, S. J., Stone, M. O. (2002) Journal of nanoscience and nantechnology 2: 95-100
Oren E E, Tamerler C, Sarikaya M.1: Nano Lett. 2005 March; 5(3):415-9. Metal recognition of septapeptides via polypod molecular architecture.
Sanghvi, A. B., Miller, K., Belcher, M. A., Schmidt, C. (2005) Nature Materials 4: 496-502
Sano, K. and Shiba, K. (2003) J. Am. Chem. Soc. 125: 14234-14235
Schembri, M. A., Kjaergaard, K. K., Klemm, P. (1999) FEMS Microbial Lett. 170, 363-371
Tamerler, C. and Sarikaya, M. (2007) Acta Biomaterialia 3(3): 289-99.
Wang, S., Humphreys, E., Jagota, A. (2003) Nature Materials 2: 196-200
Zuo, R., Ornek, D., Wood, T. (2005) Appl. Microbiol. Biotechnol. 68: 505-509
Kjaergaard, K., Sorensen, J., Schembri, M., Klemm, P. (2000). Applied and environmental Microbiology, 2000, 10-14.
Dincer S, Tamerler C, Oren E E, Sarikaya M, unpublished data.
Whaley S., English, D., Hu, E., Barbara, P., Belcher, A. (2000) Nature, 405, 665-668.
Xu, Z., Jinchun, C., Peng, Y., Wantai, Y. (2005). J. Inorg. Biochem. (99), 1692-1697.

The invention claimed is:

1. A method of separating inorganic powder particles from a mixture of powder particles, comprising:
   (a) contacting the mixture of powder particles, wherein the mixture of powder particles comprises stainless steel powder particles and at least one different inorganic powder particle, with an inorganic-binding peptide having SEQ ID NO: 31 attached to a solid support, wherein the stainless steel powder particles bind to the inorganic-binding peptide having SEQ ID NO: 31; or
   contacting the mixture of powder particles, wherein the mixture of powder particles comprises titanium dioxide (TiO₂) powder particles and at least one different inorganic powder particle, with an inorganic-binding peptide having SEQ ID NO: 32 attached to a solid support, wherein the TiO₂ powder particles bind to the inorganic-binding peptide having SEQ ID NO: 32; and
   (c) separating the stainless steel powder particles bound to the inorganic-binding peptide having SEQ ID NO: 31 attached to the solid support from the at least one different inorganic powder particle; or
   separating the TiO₂ powder particles bound to the inorganic-binding peptide having SEQ ID NO: 32 attached to the solid support, wherein the at least one different inorganic powder particle comprises at least one material selected from the group consisting of aluminum, antimony, beryllium, cadmium, copper, chrome, gold, iron, lead, selenium, palladium, platinum, stainless steel, titanium, zinc, silicon, germanium, carbon, and oxides thereof.

2. The method of claim 1, wherein the solid support is a magnetic bead.

3. The method of claim 1, further comprising c) removing the inorganic binding peptide from the stainless steel powder particles, or removing the inorganic binding peptide from the TiO₂ powder particles.

4. The method of claim 1, wherein the mixture of powder particles comprise a nanopowder.

* * * * *